United States Patent
Amrein et al.

(10) Patent No.: US 7,507,733 B2
(45) Date of Patent: Mar. 24, 2009

(54) 11B-HSD1 INHIBITORS FOR THE TREATMENT OF DIABETES

(75) Inventors: Kurt Amrein, Itingen (CH); Daniel Hunziker, Moehlin (CH); Bernd Kuhn, Liestal (CH); Alexander Mayweg, Loerrach (DE); Werner Neidhart, Hagenthal le Bas (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 499 days.

(21) Appl. No.: 11/168,031

(22) Filed: Jun. 27, 2005

(65) Prior Publication Data
US 2005/0288308 A1 Dec. 29, 2005

(30) Foreign Application Priority Data
Jun. 28, 2004 (EP) ................... 04102999

(51) Int. Cl.
*C07D 239/69* (2006.01)
*A61K 31/505* (2006.01)

(52) U.S. Cl. ................... 514/235.8; 514/256; 544/122; 544/327; 544/328

(58) Field of Classification Search ................. 544/122, 544/327, 328; 514/235.8, 256
See application file for complete search history.

(56) References Cited

U.S. PATENT DOCUMENTS

| 3,670,077 A | * | 6/1972 | Freeman et al. ............... 514/86 |
| 5,420,129 A | | 5/1995 | Breu et al. |
| 5,541,186 A | | 7/1996 | Breu et al. |

FOREIGN PATENT DOCUMENTS

| EP | 0 379 806 | 8/1990 |
| EP | 0 601 386 | 6/1994 |
| EP | 0 633 259 | 1/1995 |
| JP | 2545200 | 10/1996 |
| WO | WO 01/90091 | 11/2001 |
| WO | WO 03/099773 | 12/2003 |
| WO | WO 2005/103022 | * 11/2005 |

OTHER PUBLICATIONS

Alcaraz et al., Novel N-aryl and N-heteroaryl sulfamide synthesis via palladium cross-coupling, Organic Letters, 6(16), pp. 2705-2708, 2004.*
Walker et al. 1995; J. Clin. Endocrinol. Metab. 80, 31155-3159.
P.M. Stewart and Z.S. Krozowski, Vitam. Horm. 57 (1999), pp. 249-324.
Kotelevtsev Y. et al., Proc Natl Acad Sci U S A. Dec. 23, 1997;94(26):14924-9.
Masuzaki H. et al., J Clin Invest. Jul. 2003;112(1):83-90.
Rauz S. et al., QJM. Jul. 2003;96(7):481-90.
Sandeep TC. et al., Proc Natl Acad Sci U S A. Apr. 27, 2004;101(17):6734-9.
Chemical Abstracts Service, Columbus, Ohio, US; RN:439108-35-7 (2002), XP002361362.
Chemical Abstracts Service, Columbus, Ohio, US; RN:439108-36-8 (2002), XP002361363.
Chemical Abstracts Service, Columbus, Ohio, US; RN:478039-74-6 (2003), XP002361364.
Chemical Abstracts Service, Columbus, Ohio, US; RN:478046-56-9 (2003), XP002361365.
Database-Accession No. 261666, XP002361366 & Justus Liebigs Ann. Chem., vol. 580 (1953), pp. 225-233.

* cited by examiner

*Primary Examiner*—Deepak Rao
(74) *Attorney, Agent, or Firm*—George W. Johnston; Dennis P. Tramaloni; Samuel H. Megerditchian

(57) ABSTRACT

Compounds of the formula (I):

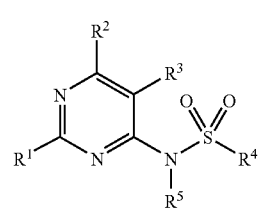

as well as pharmaceutically acceptable salts and esters thereof, wherein $R^1$ to $R^5$ have the significance given in claim 1 can be used in the form of pharmaceutical compositions.

18 Claims, No Drawings

11B-HSD1 INHIBITORS FOR THE TREATMENT OF DIABETES

FIELD OF THE INVENTION

The present invention is directed to novel pyrimidine derivatives useful as 11b-HSD1 inhibitors (T2D).

The invention is concerned particularly with compounds of formula I:

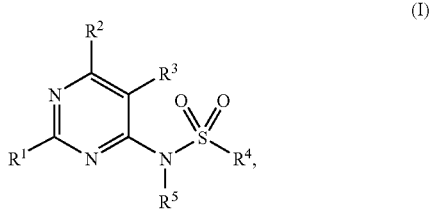

and pharmaceutically acceptable salts and esters thereof.

All documents cited or relied upon below are expressly incorporated herein by reference.

BACKGROUND OF THE INVENTION

Glucocorticoids (cortisol in humans, corticosterone in mice and rats) are an important class of adrenocorticosteroids that regulate many metabolic and homeostatic processes and form a key component of the response to stress. Glucocorticoids act via intracellular glucocorticoid receptors and, in some tissues, mineralocorticoid receptors; both being nuclear transcription factors. Glucocorticoid action on target tissues depends not only on circulating steroid concentrations and the cellular expression of receptors, but also on intracellular enzymes that critically determine to which extent glucocorticoids gain access to receptors in an active form. 11beta-hydroxysteroid dehydrogenases (11beta-HSD's) catalyze the interconversion of the principal active 11-hydroxy-glucocorticoid (cortisol) and their inactive 11-keto metabolites (cortisone).

The enzyme 11beta-hydroxysteroid dehydrogenase type 1 (11beta-HSD1) inter-converts inactive into active glucocorticoids, thereby playing a major role in local modulation of cellular agonist concentration and thus activation of corticosteroid receptors in target tissues. In a recent study made by F. Hoffmann-La Roche, differences in gene expression in lean and obese men were analyzed using gene array technology in order to identify specific changes in gene expression that might be associated with insulin resistance or altered metabolism. This study revealed that the mRNA for 11beta-HSD1 is approximately two-fold up regulated in adipose tissue in obese individuals. Moreover, overexpressing 11beta-HSD1 in adipocytes of mice led to visceral obesity and to a syndrome-X like phenotype (Masuzaki H. et al., Science. 2001 Dec. 7; 294(5549):2166-70.). Taken together, this data very strongly supports an important role of 11beta-HSD1 in the induction of obesity and the impairment of glucose homeostasis and lipid parameters. Thus, selective inhibition of this enzyme could lower blood glucose levels in Type 2 diabetic patients, normalize elevated lipid parameters and/or reduce weight in obese subjects.

The first pharmacological indication that 11beta-HSD1 inhibition in humans might have beneficial effects was obtained by using carbenoxolone, an anti-ulcer drug which inhibits both 11beta-HSD1 and the related enzyme 11beta-HSD2. Treatment with carbenoxolone led to an increase in insulin sensitivity indicating that that inhibition of 11beta-HSD1 may reduce cellular cortisol levels and therefore minimizing some of its deleterious effects. (Walker et al. 1995; J. Clin. Endocrinol. Metab. 80, 31155-3159).

11beta-HSD1 is expressed in many tissues including liver, adipose tissue, vascular smooth muscles, pancreas and brain. Its activity is dependent on NADP(H) and it has a relatively low affinity for its substrate (compared to 11beta-HSD2). 11 beta-HSD1 in tissue homogenates and when purified is bidirectional, exhibiting both 11beta-dehydrogenase and 11beta-reductase reactions, with greater stability of the dehydrogenase activity (P. M. Stewart and Z. S. Krozowski, Vitam. Horm. 57 (1999), pp. 249-324). However, when the enzyme activity is tested in intact cells, the 11beta-reductase activity predominates, which regenerates active glucocorticoids from inert 11-keto forms. Such glucocorticoid regeneration will increase effective intracellular glucocorticoid levels and, thereby, amplify glucocorticoid activity. It is this elevated cellular cortisol concentration that might lead to increased hepatic glucose production, adipocyte differentiation and insulin resistance.

Inhibition of 11beta-HSD1 should not only reduce the typical Syndrome-X/Diabetes associated symptoms, but it should also be safe and without major side effect. Studies with the unspecific inhibitor carbenoxolone highlight the importance of developing specific 11beta-HSD1 inhibitors. The inhibition of the 11beta-HSD2 enzyme is badly tolerated and results in increased blood pressure. By contrast, inhibition of 11beta-HSD1 should be well tolerated since 11beta-HSD1 knockout mice were found be healthy and to resist hyperglycemia provoked by obesity or stress (Kotelevtsev Y. et al., Proc Natl Acad Sci USA. 1997 Dec. 23; 94(26):14924-9). Similar upon starvation these mice had attenuated activation of key hepatic enzymes that are involved in gluconeogenesis. In addition, these mice had improved lipid and lipoprotein profiles suggesting that inhibition of HSD1 might be highly efficacious and safe. Recent reports indicate that 11beta-HSD1 inhibitors might also be beneficial to reduce high blood pressure (Masuzaki H. et al., J Clin Invest. 2003 July; 112(1): 83-90; Rauz S. et al., QJM. 2003 July; 96(7):481-90) to improve cognition (Sandeep T C. et al., Proc Natl Acad Sci USA. 2004 Apr. 27; 101(17):6734-9) or to improve Alzheimer associated deficits. A need exists in the art, therefore, for 11beta-HSD1 inhibitors as a safe and efficacious approach to treat diabetes, obesity and other diseases.

SUMMARY OF THE INVENTION

In one embodiment of the present invention, provided is a compound of the formula (I):

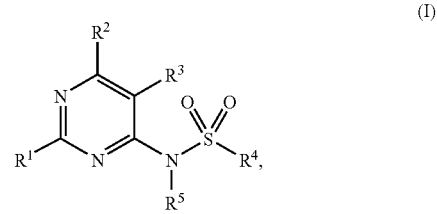

wherein:

R¹ is alkyl, cycloalkyl, cycloalkylalkoxy, alkoxyalkyl, cycloalkylalkoxyalkyl, heterocyclyl, heterocyclylalkyl, aryl, arylalkyl, aryloxyalkyl, amino or aminoalkyl;

R² is hydrogen, alkyl or aryl;

R³ is hydrogen, alkyl or aryl;

R⁴ is phenyl, naphtyl, thiophenyl, quinolyl, piperidyl, morpholyl or thiomorpholyl, wherein phenyl, naphtyl, thiophenyl, quinolyl, piperidyl, morpholyl and thiomorpholyl are optionally substituted with one or more substituents independently selected from alkyl, cycloalkyl, halogen, alkoxy, cyano, trifluoromethyl, aryl, arylalkyl, aryloxy, oxazolyl, pyridinyl, pyrimidinyl, pyrazolyl, imidazolyl and thiazolyl;

R⁵ is hydrogen, alkyl, aralkyl, cycloalkylalkyl or aminocarbonylalkyl;

and pharmaceutically acceptable salts and esters thereof, and, wherein

N-(2,6-dimethyl-4-pyrimidinyl)-benzenesulfonamide;

2-chloro-N-(2-methyl-4-pyrimidinyl)-p-toluenesulfonamide;

N-(2-(dimethylamino)-6-methyl-5-propyl-4-pyrimidinyl)-benzenesulfonamide; and 2,4,5-trichloro-N-(2,6-dimethyl-4-pyrimidinyl)-benzene-sulfonamide are excluded.

In another embodiment of the present invention, provided is a process for the preparation of a compound of the formula (I), comprising the reaction of a compound according to formula

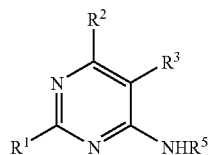

A in the presence of a compound according to formula

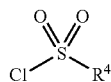

wherein R¹ to R⁵ are defined above.

In a further embodiment of the present invention, provided is a pharmaceutical composition comprising a therapeutically effective amount of a compound of the formula (I) and a therapeutically inert carrier.

In a still another embodiment of the present invention, provided is a method for the treatment and prophylaxis of diabetes, obesity, eating disorders, dyslipidemiae and hypertension, comprising the step of administering a therapeutically effective amount of a compound of the formula (I) to a patient in need thereof.

DETAILED DESCRIPTION

The compounds of formula I and their pharmaceutically acceptable salts and esters are novel and have valuable pharmacological properties. In particular they are 11b-HSD1 inhibitors (T2D) and they display selectivity against the related 11beta-HSD2 enzyme. Therefore the compounds which are specific 11beta-HSD1 inhibitors (T2D) represent an approach to e.g. lower blood glucose levels and normalize lipid parameters in Type 2 diabetic patients by modulating the local concentration of the active glucocorticoid cortisol in target tissue (liver, adipose tissue).

The compounds of the present invention can be used in the prophylaxis and/or treatment of metabolic disorders, obesity, dyslipidemiae, hypertension and/or diabetes, particularly diabetes Type II.

The compounds of this invention can further be used in the prophylaxis and/or treatment of high ocular eye pressure, cognition, Alzheimer and/or neurodegeneration.

The compounds of the present invention can further be combined with PPAR (alpha, gamma, delta) agonists, DHEA (dehydroepiandrosterone), DPPIV inhibitors, insulin and/or lipase inhibitors, particularly orlistat.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of $C_3$-$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec.butoxy and tert.butoxy, preferably methoxy and ethoxy and most preferred methoxy.

The term "aryl", alone or in combination, signifies a phenyl or naphthyl group, preferably a phenyl group which optionally carries one or more substituents, preferably one to three, each independently selected from halogen, trifluoromethyl, trifluoromethoxy, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, alkyl-$SO_2$—, amino-$SO_2$—, cycloalkyl and the like. Preferred is phenyl or naphthyl, particularly phenyl optionally substituted with one to three, preferably one or two substituents independently selected from alkyl, halogen, alkoxy, trifluoromethoxy, nitro and trifluoromethyl. Particularly preferred is phenyl.

The term "aryloxy", alone or in combination, signifies a aryl-O— group in which the term "aryl" has the previously given significance.

The term "aralkyl", alone or in combination, signifies a arylalkyl group in which the terms "aryl" and "alkyl" have the previously given significance.

The term "heterocyclyl", alone or in combination signifies a saturated, partially unsaturated or aromatic 5- to 10-membered heterocycle which contains one or more hetero atoms selected from nitrogen, oxygen and sulphur. If desired, it can be substituted on one or more carbon atoms e.g. by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl- or on a tertiary nitrogen atom (i.e. =N—) by oxido, with halogen, alkyl, cycloalkyl and alkoxy being preferred. Examples of such heterocyclyl groups are pyrrolidinyl, piperidinyl, piperazinyl, morpholinyl, thiomorpholinyl, pyrazoyl, imidazoyl (e.g. imidazol-4-yl and 1-benzyloxycarbonyl-imidazol-4-yl), pyrazoyl, pyridyl, pyrazinyl, pyrimidinyl, hexahydro-pyrimidinyl, furyl, thienyl, thiazolyl, oxazolyl, indolyl (e.g. 2-indolyl), quinolyl (e.g. 2-quinolyl, 3-quinolyl and 1-oxido-2-quinolyl), isoquinolyl (e.g. 1-isoquinolyl and 3-isoquinolyl), tetrahydroquinolyl (e.g. 1,2,3,4-tetrahydro-2-quinolyl), 1,2,3,4-tetrahydroisoquinolyl (e.g. 1,2,3,4-tetrahydro-1-oxo-isoquinolyl) and quinoxalinyl. Preferred examples are thiophenyl, quinolyl, piperidyl, morpholyl, thiomorpholyl, oxazolyl, pyridinyl, pyrimidinyl, pyrazolyl, imidazolyl and thiazolyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —$NH_2$, methylamino, ethylamino, dimethylamino, diethylamino, methyl-ethylamino, pyrrolidin-1-yl or piperidino etc., preferably primary amino, dimethylamino and diethylamino and particularly dimethylamino.

The term "halogen", alone or in combination, signifies fluorine, chlorine, bromine or iodine and preferably fluorine, chlorine or bromine.

The term "carbonyl", alone or in combination, signifies the —C(O)— group.

The term "oxy", alone or in combination, signifies the —O— group.

The term "nitro", alone or in combination signifies the —$NO_2$ group.

The term "cyano", alone or in combination signifies the group —CN.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Pharmaceutically acceptable esters" means that compounds of general formula (I) may be derivatized at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

Preferred are the compounds of formula I and pharmaceutically acceptable salts thereof, particularly the compounds of formula I.

Preferred are those compounds of formula I, wherein $R^1$ is alkyl, cycloalkyl, alkoxyalkyl, cycloalkylalkoxyalkyl, heterocyclyl, heterocyclylalkyl, aryl, arylalkyl, aryloxyalkyl, amino or aminoalkyl;

$R^2$ is hydrogen or alkyl;

$R^3$ is hydrogen or alkyl;

$R^4$ is phenyl, naphtyl, thiophenyl, quinolyl, piperidyl, morpholyl or thiomorpholyl, wherein phenyl, naphtyl, thiophenyl, quinolyl, piperidyl, morpholyl and thiomorpholyl are optionally substituted with one or more substituents independently selected from alkyl, cycloalkyl, halogen, alkoxy, cyano, trifluoromethyl, aryl, arylalkyl, aryloxy, oxazolyl, pyridinyl, pyrimidinyl, pyrazolyl, imidazolyl and thiazolyl;

$R^5$ is hydrogen or alkyl;

and pharmaceutically acceptable salts and esters thereof; and, wherein

N-(2,6-dimethyl-4-pyrimidinyl)-benzenesulfonamide;

2-chloro-N-(2-methyl-4-pyrimidinyl)-p-toluenesulfonamide;

N-(2-(dimethylamino)-6-methyl-5-propyl-4-pyrimidinyl)-benzenesulfonamide; and 2,4,5-trichloro-N-(2,6-dimethyl-4-pyrimidinyl)-benzenesulfonamide are excluded.

Further preferred are compounds according to formula I, wherein $R^1$ is alkyl, cycloalkyl, alkoxyalkyl, cycloalkylalkoxyalkyl, heterocyclyl, heterocyclylalkyl or aryl.

Particularly preferred are compounds according to formula I, wherein $R^1$ is methyl, ethyl, cyclopropoyl, cyclobutyl, isopropyl, tert.butyl, methoxymethyl, cyclopropylmethoxymethyl, 2-methyl-thiazolyl, morpholinylmethyl or phenyl.

Also preferred are compounds of formula I, wherein $R^2$ is hydrogen.

Another preferred object of the present invention are compounds according to formula I, wherein $R^2$ is methyl.

Preferred are compounds of formula I, wherein $R^3$ is hydrogen.

Another preferred aspect of the present invention are compounds according to formula I, wherein $R^5$ is hydrogen.

Further preferred are compounds according to formula I, wherein $R^5$ is methyl.

Also preferred are compounds of formula I, wherein $R^4$ is phenyl, naphtyl, thiophenyl, quinolyl or piperidyl, wherein phenyl, naphtyl, thiophenyl, quinolyl and piperidyl are optionally substituted with one or more, preferably one to three substituents independently selected from alkyl, halogen, alkoxy, trifluoromethyl, aryl, oxazolyl and pyridinyl.

Further preferred are compounds of formula I, wherein $R^4$ is phenyl substituted with one or more, preferably one to three substituents independently selected from alkyl, cycloalkyl, halogen, alkoxy, trifluoromethyl, phenyl and oxazolyl.

Preferred are compounds of formula I, wherein $R^4$ is phenyl, naphtyl, quinolyl or piperidyl.

Also preferred are compounds of formula I, wherein $R^4$ is thiophenyl, morpholyl or thiomorpholyl, wherein thiophenyl, morpholyl and thiomorpholyl are optionally substituted with one or more, preferably one to three substituents independently selected from alkyl, cycloalkyl, halogen, alkoxy, cyano, trifluoromethyl, aryl, arylalkyl, aryloxy, oxazolyl, pyridinyl, pyrimidinyl, pyrazolyl, imidazolyl and thiazolyl.

Examples of preferred compounds of formula (I) are:
1. 3-Chloro-2-methyl-N-(2-methyl-pyrimidin-4-yl)-benzenesulfonamide;
2. 3-Chloro-N-(2-cyclopropyl-pyrimidin-4-yl)-2-methyl-benzenesulfonamide;
3. N-(2-Cyclopropyl-pyrimidin-4-yl)-2,5-difluoro-benzenesulfonamide;
4. Naphthalene-2-sulfonic acid (2-cyclopropyl-pyrimidin-4-yl)-amide;
5. Biphenyl-4-sulfonic acid (2-cyclopropyl-pyrimidin-4-yl)-amide;
6. Quinoline-8-sulfonic acid (2-cyclopropyl-pyrimidin-4-yl)-amide;
7. N-(2-Cyclopropyl-pyrimidin-4-yl)-benzenesulfonamide;
8. N-(2-Cyclopropyl-pyrimidin-4-yl)-5-fluoro-2-methyl-benzenesulfonamide;
9. N-(2-Cyclopropyl-pyrimidin-4-yl)-3-methoxy-benzenesulfonamide;
10. N-(2-Cyclopropyl-pyrimidin-4-yl)-2-methoxy-5-methyl-benzenesulfonamide;
11. 3-Chloro-N-(2-cyclopropyl-pyrimidin-4-yl)-4-methoxy-benzenesulfonamide;
12. 5-Chloro-N-(2-cyclopropyl-pyrimidin-4-yl)-2-methoxy-benzenesulfonamide;
13. 5-Fluoro-N-(2-isopropyl-pyrimidin-4-yl)-2-methyl-benzenesulfonamide;
14. 3,4-Dichloro-N-(2-isopropyl-pyrimidin-4-yl)-benzenesulfonamide;
15. N-(2-Isopropyl-pyrimidin-4-yl)-4-(1.3-oxazol-5-yl)-benzenesulfonamide;
16. 2,4-Dichloro-N-(2-isopropyl-pyrimidin-4-yl)-6-methyl-benzenesulfonamide;
17. 2,3-Dichloro-N-(2-isopropyl-pyrimidin-4-yl)-benzenesulfonamide;
18. 4,5-Dichloro-thiophene-2-sulfonic acid (2-isopropyl-pyrimidin-4-yl)-amide;
19. 5-Pyridin-2-yl-thiophene-2-sulfonic acid (2-isopropyl-pyrimidin-4-yl)-amide;
20. 3-Chloro-N-(2-isopropyl-pyrimidin-4-yl)-2-methyl-benzenesulfonamide;
21. N-(2-Isopropyl-pyrimidin-4-yl)-3-trifluoromethyl-benzenesulfonamide;
22. N-(2-Isopropyl-pyrimidin-4-yl)-2-trifluoromethyl-benzenesulfonamide;
23. 5-Chloro-thiophene-2-sulfonic acid (2-isopropyl-pyrimidin-4-yl)-amide;
24. N-(2-Isopropyl-pyrimidin-4-yl)-4-trifluoromethyl-benzenesulfonamide;
25. Piperidine-1-sulfonic acid (2-isopropyl-pyrimidin-4-yl)-amide;
26. Naphthalene-2-sulfonic acid (2-isopropyl-pyrimidin-4-yl)-amide;
27. Biphenyl-4-sulfonic acid (2-isopropyl-pyrimidin-4-yl)-amide;
28. 2,5-Difluoro-N-(2-isopropyl-pyrimidin-4-yl)-benzenesulfonamide;
29. N-(2-Isopropyl-pyrimidin-4-yl)-3,4-dimethoxy-benzenesulfonamide;
30. N-(2-tert-Butyl-pyrimidin-4-yl)-3,4-dichloro-benzenesulfonamide;
31. N-(2-tert-Butyl-pyrimidin-4-yl)-5-fluoro-2-methyl-benzenesulfonamide;
32. Naphthalene-2-sulfonic acid (2-tert-butyl-pyrimidin-4-yl)-amide;
33. N-(2-tert-Butyl-pyrimidin-4-yl)-2,5-difluoro-benzenesulfonamide;
34. N-(2-tert-Butyl-pyrimidin-4-yl)-4-(1.3-oxazol-5-yl)-benzenesulfonamide;
35. 3-Chloro-N-(2-ethyl-pyrimidin-4-yl)-2-methyl-benzenesulfonamide;
36. 2,4-Dichloro-N-(2-ethyl-pyrimidin-4-yl)-6-methyl-benzenesulfonamide;
37. 4-Chloro-N-(2-ethyl-pyrimidin-4-yl)-2,5-dimethyl-benzenesulfonamide;
38. 3-Chloro-N-(2-cyclobutyl-pyrimidin-4-yl)-2-methyl-benzenesulfonamide;
39. Naphthalene-2-sulfonic acid (2-cyclobutyl-pyrimidin-4-yl)-amide;
40. 5-Pyridin-2-yl-thiophene-2-sulfonic acid (2-cyclobutyl-pyrimidin-4-yl)-amide;
41. 2,4-Dichloro-N-(2-cyclobutyl-pyrimidin-4-yl)-6-methyl-benzenesulfonamide;
42. 3,4-Dichloro-N-(2-methoxymethyl-pyrimidin-4-yl)-benzenesulfonamide;
43. 3-Chloro-N-(2-cyclopropylmethoxymethyl-pyrimidin-4-yl)-2-methyl-benzenesulfonamide;
44. 3-Chloro-2-methyl-N-(2-morpholin-4-ylmethyl-pyrimidin-4-yl)-benzenesulfonamide;
45. Naphthalene-2-sulfonic acid (2,6-dimethyl-pyrimidin-4-yl)-amide;
46. 3-Chloro-N-(2-cyclopropyl-pyrimidin-4-yl)-2-N-dimethyl-benzenesulfonamide;
47. 3,4-Dichloro-N-(2-isopropyl-pyrimidin-4-yl)-N-methyl-benzenesulfonamide;
48. 3-Chloro-2-methyl-N-(2-phenyl-pyrimidin-4-yl)-benzenesulfonamide; and
49. 3-Chloro-2-methyl-N-[2-(2-methyl-thiazol-4-yl)-pyrimidin-4-yl]-benzenesulfonamide.

Further examples of preferred compounds are
50. 3-Chloro-N-(2-methoxymethyl-pyrimidin-4-yl)-2-methyl-benzenesulfonamide;
51. Naphthalene-2-sulfonic acid (2,5,6-trimethyl-pyrimidin-4-yl)-amide;
52. 4,5-Dichloro-2-fluoro-N-(2-isopropyl-pyrimidin-4-yl)-benzenesulfonamide;
53. 2,4-Difluoro-N-(2-isopropyl-pyrimidin-4-yl)-benzenesulfonamide;
54. 2-Chloro-N-(2-isopropyl-pyrimidin-4-yl)-benzenesulfonamide;
55. 4-Chloro-N-(2-isopropyl-pyrimidin-4-yl)-benzenesulfonamide;
56. 3-Chloro-N-(2-isopropyl-pyrimidin-4-yl)-benzenesulfonamide;
57. 2,4-Dichloro-N-(2-isopropyl-pyrimidin-4-yl)-benzenesulfonamide;
58. 2,4-Dichloro-N-(2-isopropyl-pyrimidin-4-yl)-5-methyl-benzenesulfonamide;
59. 2,5-Dichloro-N-(2-isopropyl-pyrimidin-4-yl)-benzenesulfonamide;

60. 3-Bromo-5-chloro-thiophene-2-sulfonic acid (2-isopropyl-pyrimidin-4-yl)-amide;
61. 2,4-Dichloro-N-(2-cyclopropyl-pyrimidin-4-yl)-6-methyl-benzenesulfonamide;
62. 4-Chloro-N-(2-cyclopropyl-pyrimidin-4-yl)-2,5-dimethyl-benzenesulfonamide;
63. N-(2-Cyclopropyl-pyrimidin-4-yl)-2,4-dimethoxy-benzenesulfonamide;
64. 3-Chloro-N-(2-cyclopentyl-pyrimidin-4-yl)-2-methyl-benzenesulfonamide;
65. 5-Phenyl-thiophene-2-sulfonic acid (2-cyclopropyl-pyrimidin-4-yl)-amide;
66. 3-Chloro-N-(2-cyclopropylmethoxy-pyrimidin-4-yl)-2-methyl-benzenesulfonamide;
67. 2-[(3,4-Dichloro-benzenesulfonyl)-(2-isopropyl-pyrimidin-4-yl)-amino]-N,N-dimethyl-acetamide;
68. N-Benzyl-3-chloro-N-(2-cyclopropyl-pyrimidin-4-yl)-2-methyl-benzenesulfonamide;
69. 3-Chloro-N-cyclopropylmethyl-N-(2-cyclopropyl-pyrimidin-4-yl)-2-methyl-benzenesulfonamide and
70. 3-Chloro-2-methyl-N-(6-phenyl-pyrimidin-4-yl)-benzenesulfonamide.

Examples of particularly preferred compounds of formula (I) are:
3-Chloro-2-methyl-N-(2-methyl-pyrimidin-4-yl)-benzenesulfonamide;
3-Chloro-N-(2-cyclopropyl-pyrimidin-4-yl)-2-methyl-benzenesulfonamide;
N-(2-Cyclopropyl-pyrimidin-4-yl)-2,5-difluoro-benzenesulfonamide;
Naphthalene-2-sulfonic acid (2-cyclopropyl-pyrimidin-4-yl)-amide;
Biphenyl-4-sulfonic acid (2-cyclopropyl-pyrimidin-4-yl)-amide;
5-Fluoro-N-(2-isopropyl-pyrimidin-4-yl)-2-methyl-benzenesulfonamide;
3,4-Dichloro-N-(2-isopropyl-pyrimidin-4-yl)-benzenesulfonamide;
N-(2-Isopropyl-pyrimidin-4-yl)-4-(1.3-oxazol-5-yl)-benzenesulfonamide;
2,4-Dichloro-N-(2-isopropyl-pyrimidin-4-yl)-6-methyl-benzenesulfonamide;
2,3-Dichloro-N-(2-isopropyl-pyrimidin-4-yl)-benzenesulfonamide;
5-Pyridin-2-yl-thiophene-2-sulfonic acid (2-isopropyl-pyrimidin-4-yl)-amideyes;
3-Chloro-N-(2-isopropyl-pyrimidin-4-yl)-2-methyl-benzenesulfonamide;
N-(2-Isopropyl-pyrimidin-4-yl)-3-trifluoromethyl-benzenesulfonamide;
N-(2-Isopropyl-pyrimidin-4-yl)-2-trifluoromethyl-benzenesulfonamide;
5-Chloro-thiophene-2-sulfonic acid (2-isopropyl-pyrimidin-4-yl)-amide; //////
N-(2-Isopropyl-pyrimidin-4-yl)-4-trifluoromethyl-benzenesulfonamide;
Naphthalene-2-sulfonic acid (2-isopropyl-pyrimidin-4-yl)-amide;
Biphenyl-4-sulfonic acid (2-isopropyl-pyrimidin-4-yl)-amide;
2,5-Difluoro-N-(2-isopropyl-pyrimidin-4-yl)-benzenesulfonamide;
N-(2-Isopropyl-pyrimidin-4-yl)-3,4-dimethoxy-benzenesulfonamide;
N-(2-tert-Butyl-pyrimidin-4-yl)-4-oxazol-5-yl-benzenesulfonamide;
3-Chloro-N-(2-ethyl-pyrimidin-4-yl)-2-methyl-benzenesulfonamide;
2,4-Dichloro-N-(2-ethyl-pyrimidin-4-yl)-6-methyl-benzenesulfonamide;
3-Chloro-N-(2-cyclobutyl-pyrimidin-4-yl)-2-methyl-benzenesulfonamide;
Naphthalene-2-sulfonic acid (2-cyclobutyl-pyrimidin-4-yl)-amide;
5-Pyridin-2-yl-thiophene-2-sulfonic acid (2-cyclobutyl-pyrimidin-4-yl)-amide;
2,4-Dichloro-N-(2-cyclobutyl-pyrimidin-4-yl)-6-methyl-benzenesulfonamide;
3-Chloro-N-(2-cyclopropyl-pyrimidin-4-yl)-2-N-dimethyl-benzenesulfonamide; and
3,4-Dichloro-N-(2-isopropyl-pyrimidin-4-yl)-N-methyl-benzenesulfonamide.

The preparation of compounds of formula I of the present invention may be carried out in sequential or convergent synthetic routes. Syntheses of the invention are shown in the following Schemes. The skills required for carrying out the reaction and purification of the resulting products are known to those in the art. The substituents and indices used in the following description of the processes have the significance given above unless indicated to the contrary.

In general, compounds of type I are readily accessible by sulfonylation of appropriately substituted 4-amino-pyrimidines A with sulfonyl chlorides under various conditions that are known to persons skilled in the art. Examples of such conditions are—as indicated in the scheme below—e.g. pyridine at elevated temperatures or THF under reflux conditions in the presence of a base such as potassium carbonate, sodium carbonate, sodium hydride, triethyl amine or the like.

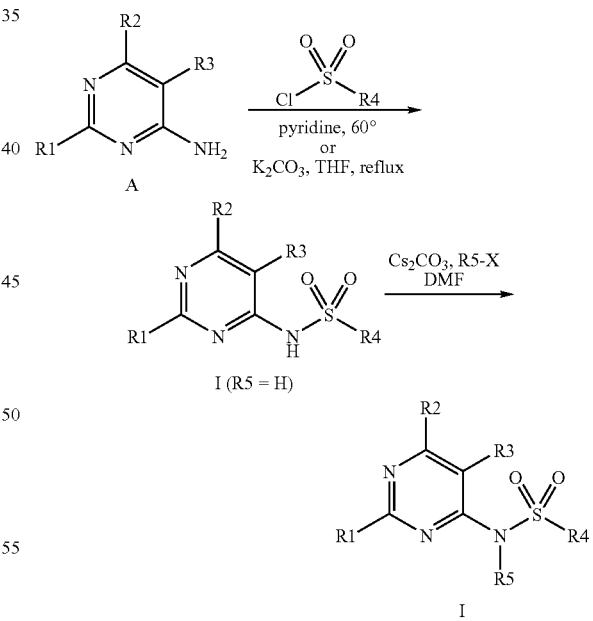

Compounds I with R5=H obtained in this way can optionally be further substituted at the sulfonamide nitrogen by treatment with a base such as sodium hydride, cesium carbonate, potassium carbonate or the like in a solvent such as DMF or THF followed by alkylation of the resulting anion with an alkylhalide such as methyl iodide, ethyl bromide, benzyl bromide or the like in order to introduce the desired R5 substituent.

Appropriately substituted 4-amino-pyrimidines A are either commercially available, known in the literature or can be made in analogy to literature procedures from known starting materials. A convenient synthesis uses amidines or amidine salts B as starting materials that are—after liberation of the free amidine by treatment with a base such as triethyl amine, sodium ethoxide, potassium carbonate or the like if amidine salts are used as starting materials—treated with an acrylonitrile such as 2-chloro-acrylonitrile or 3-ethoxy-acrylonitrile under conditions that have been described earlier (e.g. J. Heterocyclic Chem. 14, 1977, 1413-1414). Other, alternative approaches for the preparation of appropriately substituted 4-amino-pyrimidines are also available form the literature.

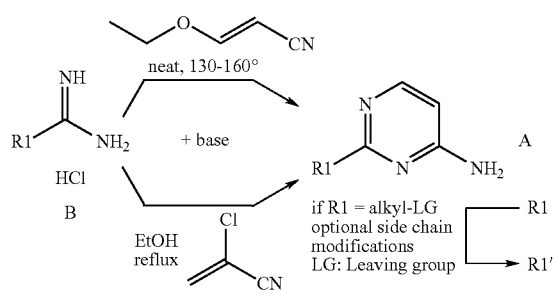

In the presence of an appropriately substituted side chain at position 2 of the 4-amino-pyrimidine intermediate A, e.g. in case of the presence of a leaving group such as a halide in the side chain, additional but optional modifications are possible. For example, the leaving group may be exchanged by treatment of the appropriate starting material with a) alcohols and a base to furnish aryl- or alkyl ethers, or b) amines to provide aminoalkyl derivatives as illustrated in Scheme A below. When the leaving group is attached directly to the pyrimidine nucleus in position 2, reactions with alcohols are possible in similar manner to give O-substituted 2-hydroxy-4-aminopyrimidines (Scheme B).

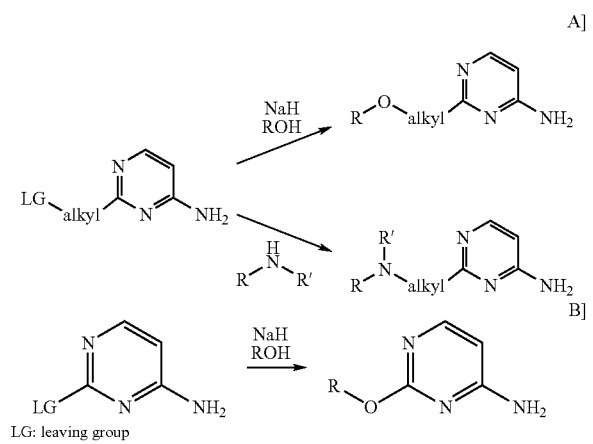

The conversion of a compound of formula I into a pharmaceutically acceptable salt can be carried out by treatment of such a compound with an inorganic acid, for example a hydrohalic acid, such as, for example, hydrochloric acid or hydrobromic acid, sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid. The corresponding carboxylate salts can also be prepared from the compounds of formula I by treatment with physiologically compatible bases.

The conversion of compounds of formula I into pharmaceutically acceptable esters or amides can be carried out e.g. by treatment of suited amino or hydroxyl groups present in the molecules with an carboxylic acid such as acetic acid, with a condensating reagent such as benzotriazol-1-yloxytris(dimethylamino)phosphonium hexafluorophosphate (BOP) or N,N-dicylohexylcarbodiimide (DCCI) to produce the carboxylic ester or carboxylic amide.

A preferred process for the preparation of a compound of formula I as defined before comprises the reaction of a compound according to formula

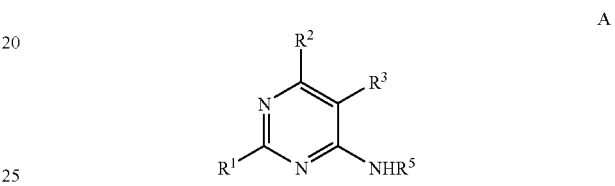

in the presence of a compound according to formula

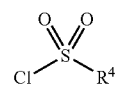

wherein $R^1$ to $R^5$ are defined as before. Particularly preferred is the above process e.g. in pyridine or THF, particularly in the presence of a base such as e.g. potassium carbonate, sodium carbonate, sodium hydride or triethyl amine. Very preferred is the above reaction in the presence of pyridine at 50° C. to 70° C. Further very preferred is the above process in the presence of THF under reflux conditions.

Preferred intermediates are:
2-Cyclopropyl-pyrimidin-4-ylamine;
2-Isopropyl-pyrimidin-4-ylamine;
2-tert-Butyl-pyrimidin-4-ylamine;
2-Ethyl-pyrimidin-4-ylamine;
2-Cyclobutyl-pyrimidin-4-ylamine;
2-Methoxymethyl-pyrimidin-4-ylamine;
2-Cyclopropylmethoxymethyl-pyrimidin-4-ylamine;
2-Morpholin-4-ylmethyl-pyrimidin-4-ylamine;
2-Phenyl-pyrimidin-4-ylamine; and
2-(2-Methyl-thiazol-4-yl)-pyrimidin-4-ylamine.

The compounds of formula I described above can be used as therapeutically active substances.

The compounds as described above can further be used for the preparation of medicaments for the prophylaxis and therapy of illnesses which are caused by disorders associated with the enzyme 11beta-hydroxysteroid dehydrogenase1 (11bHSD1).

Additionally, pharmaceutical compositions comprising a compound of the formula I as described above and a therapeutically inert carrier can be used.

A further preferred embodiment of the present invention is the use of a compound of the formula I as described above for the preparation of medicaments for the treatment and prophylaxis of diabetes, obesity, eating disorders, dyslipidemiae and hypertension.

Particularly preferred is the use of a compound according to formula I as described above for the preparation of medicaments for the treatment and prophylaxis of diabetes Type II.

Particularly preferred is a method for the treatment and prophylaxis of diabetes Type II, which method comprises administering an effective amount of a compound according to formula I as described above.

Compounds as described above have $IC_{50}$ values below 100 µM; more preferred compounds have $IC_{50}$ values below 20 µM, particularly below 5 µM. Most preferred compounds have $IC_{50}$ values below 0.5 µM.

The compounds of formula I and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically acceptable salts can be used for the prophylaxis and treatment of arthritis, cardiovascular diseases, diabetes, renal failure and particularly eating disorders and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

Example 1

3-Chloro-2-methyl-N-(2-methyl-pyrimidin-4-yl)-benzenesulfonamide

2-Methyl-pyrimidin-4-ylamine (91 mg, Gabriel, Chem. Ber. 37, 1904, 3641) and 3-chloro-2-methyl-benzenesulfonyl chloride (179 mg) were dissolved in pyridine (5 mL) and the resulting mixture was allowed to stir at 50 to 60° C. for 48 hours. The mixture was then evaporated in vacuo and the residue was dissolved in ethyl acetate. The solution was washed with 1M $CuSO_4$ solution twice, dried over $Na_2SO_4$, filtered and evaporated. The residue was purified by flash chromatography ($CH_2Cl_2$MeOH/$NH_3$ 90:10:0.5) to give the desired product 3-chloro-2-methyl-N-(2-methyl-pyrimidin-4-yl)-benzenesulfonamide as a yellow powder (22 mg). MS ($ESI^-$): 297.1 ($[M-H]^-$).

Example 2

3-Chloro-N-(2-cyclopropyl-pyrimidin-4-yl)-2-methyl-benzenesulfonamide

Step A]: 2-Cyclopropyl-pyrimidin-4-ylamine

Cyclopropylcarbamidine hydrochloride (3.0 g) was added to a solution of sodium methoxide (5.4 M, 4.61 mL) and the mixture was allowed to stir for 1 hour. The suspension was filtered in order to remove precipitated NaCl and the filtrate was evaporated in vacuo to give a light brown residue (2.86 g). 3-Ethoxyacrylonitrile (2.55 mL) was added and the mixture was heated at 135° C. for 3 hours and then allowed to stir at RT for another 12 hours. The reaction mixture was directly subjected to flash chromatography (silica gel, ethyl acetate) and the desired product 2-cyclopropyl-pyrimidin-4-ylamine was isolated as a light brown foam (1.53 g). $^1$H NMR (δ, $CDCl_3$): 8.09 (d, 1H), 6.18 (d, 1H), 4.68 (br s, 2H), 2.04-1.98 (m, 1H), 1.08-1.04 (m, 2H), 0.97-0.92 (m, 2H). MS (ESI): 136.2 ($MH^+$).

Alternative Preparation Method for Step A]:

Cyclopropylcarbamidine hydrochloride (7.61 g) was dissolved in ethanol (125 mL) and triethylamine (19.35 mL) and 2-chloro-acrylonitrile (5.52 mL) were added. The resulting orange-yellow solution was refluxed for 30 minutes. The mixture was cooled and left in a refrigerator over night. The solid was removed by filtration and the filtrate was concentrated in vacuo. The residue was purified by flash chromatography (ethyl acetate/methanol 9:1) to give 2-cyclopropyl-pyrimidin-4-ylamine (4.2 g) as a light brown solid that was still contaminated with an unidentified component, but used without further purification. $^1$H NMR (δ, DMSO-$d_6$, product signals only): 7.88 (d, 1H), 6.64 (br s, 2H), 6.16 (d, 1H), 1.89-1.82 (m, 1H), 0.87-0.81 (m, 4H).

For preparation methods for step A] see: Singh and Lesher, J. Heterocyclic Chem. 1977, 14 (8), 1413-1414

Step B]: 3-Chloro-N-(2-cyclopropyl-pyrimidin-4-yl)-2-methyl-benzenesulfonamide

This material was obtained in analogy to example 1 from 2-cyclopropyl-pyrimidin-4-ylamine (0.126 g) and 3-chloro- 2-methyl-benzenesulfonyl chloride (0.2 g) as a light yellow solid (0.067 g). MS (ESI⁻): 322.2 ([M−H]⁻).

Example 3

N-(2-Cyclopropyl-pyrimidin-4-yl)-2,5-difluoro-benzenesulfonamide

This material was obtained in analogy to example 2, steps A] and B] from 2-cyclopropyl-pyrimidin-4-ylamine (0.150 g) and 2,5-difluoro-benzenesulfonyl chloride (0.236 g) as a light yellow foam (0.1 g). MS (ESI): 312.1 (MH⁺).

Example 4

Naphthalene-2-sulfonic acid (2-cyclopropyl-pyrimidin-4-yl)-amide

This material was obtained in analogy to example 2, steps A] and B] from 2-cyclopropyl-pyrimidin-4-ylamine (0.1 g) and naphthalene-2-sulfonyl chloride (0.044 g) as a light yellow foam (0.1 g), MS (ESI⁻): 324.1 ([M−H]⁻).

Example 5

Biphenyl-4-sulfonic acid (2-cyclopropyl-pyrimidin-4-yl)-amide

This material was obtained in analogy to example 2, steps A] and B] from 2-cyclopropyl-pyrimidin-4-ylamine (0.1 g) and biphenyl-4-sulfonyl chloride (0.18 g) as a light yellow foam (0.032 g). MS (ESI⁻): 350.2 ([M−H]⁻).

Example 6

Quinoline-8-sulfonic acid (2-cyclopropyl-pyrimidin-4-yl)-amide

This material was obtained in analogy to example 2, steps A] and B] from 2-cyclopropyl-pyrimidin-4-ylamine (0.1 g) and quinoline-8-sulfonyl chloride (0.16 g) as a light yellow foam (8 mg). MS (ESI⁻): 325.1 ([M−H]⁻).

Example 7

N-(2-Cyclopropyl-pyrimidin-4-yl)-benzenesulfonamide

This material was obtained in analogy to example 2, steps A] and B] from 2-cyclopropyl-pyrimidin-4-ylamine (0.1 g) and benzenesulfonyl chloride (0.125 g) as a light yellow foam (36 mg). MS (ESI⁻): 274.0 ([M−H]⁻).

Example 8

N-(2-Cyclopropyl-pyrimidin-4-yl)-5-fluoro-2-methyl-benzenesulfonamide

This material was obtained in analogy to example 2, steps A] and B] from 2-cyclopropyl-pyrimidin-4-ylamine (0.1 g) and benzenesulfonyl chloride (0.178 g) as a light yellow foam (76 mg). MS (ESI⁻): 306.2 ([M−H]⁻).

Example 9

N-(2-Cyclopropyl-pyrimidin-4-yl)-3-methoxy-benzenesulfonamide

This material was obtained in analogy to example 2, steps A] and B] from 2-cyclopropyl-pyrimidin-4-ylamine (0.13 g) and 3-methoxy-benzenesulfonyl chloride (0.2 g) as a white foam (108 mg). MS (ESI⁻): 304.1 ([M−H]⁻).

Example 10

N-(2-Cyclopropyl-pyrimidin-4-yl)-2-methoxy-5-methyl-benzenesulfonamide

This material was obtained in analogy to example 2, steps A] and B] from 2-cyclopropyl-pyrimidin-4-ylamine (0.15 g) and 2-methoxy-5-methyl-benzenesulfonyl chloride (0.3 g) as a light brown solid (63 mg). MS (ESI⁻): 318.0 ([M−H]⁻).

Example 11

3-Chloro-N-(2-cyclopropyl-pyrimidin-4-yl)-4-methoxy-benzenesulfonamide

This material was obtained in analogy to example 2, steps A] and B] from 2-cyclopropyl-pyrimidin-4-ylamine (0.15 g) and 3-chloro-4-methoxy-benzenesulfonyl chloride (0.32 g) as a light brown solid (40 mg). MS (ESI): 340.1 (MH⁺).

Example 12

5-Chloro-N-(2-cyclopropyl-pyrimidin-4-yl)-2-methoxy-benzenesulfonamide

This material was obtained in analogy to example 2, steps A] and B] from 2-cyclopropyl-pyrimidin-4-ylamine (0.15 g) and 5-chloro-2-methoxy-benzenesulfonyl chloride (0.32 g) as a light brown solid (15 mg). MS (ESI⁻): 338.1 ([M−H]⁻).

Example 13

5-Fluoro-N-(2-isopropyl-pyrimidin-4-yl)-2-methyl-benzenesulfonamide

Step A]: 2-Isopropyl-pyrimidin-4-ylamine

This compound was made in analogy to example 2, step A] from cyclopropylcarbamidine hydrochloride (3 g) and 3-ethoxyacrylonitrile (2.5 mL) to give 2-isopropyl-pyrimidin-4-ylamine (1.36 g) as a light yellow foam. MS (ESI): 138.1 (MH⁺).

Step B]: 5-Fluoro-N-(2-isopropyl-pyrimidin-4-yl)-2-methyl-benzenesulfonamide

This material was obtained in analogy to example 1 from 2-isopropyl-pyrimidin-4-ylamine (0.13 g) and 5-fluoro-2-methylbenzenesulfonyl chloride (0.32 g) as a light yellow foam (72 mg). MS (ESI⁻): 308.1 ([M−H]⁻).

Example 14

3,4-Dichloro-N-(2-isopropyl-pyrimidin-4-yl)-benzenesulfonamide

This material was obtained in analogy to example 13 from 2-isopropyl-pyrimidin-4-ylamine (0.23 g) and 3,4-dichlorobenzenesulfonyl chloride (0.41 g) as a light yellow solid (295 mg). MS (ESI$^-$): 343.9 ([M–H]$^-$).

Example 15

N-(2-Isopropyl-pyrimidin-4-yl)-4-(1.3-oxazol-5-yl)-benzenesulfonamide

This material was obtained in analogy to example 13 from 2-isopropyl-pyrimidin-4-ylamine (0.174 g) and 4-(1.3-oxazol-5-yl)-benzenesulfonyl chloride (0.31 g) as a light yellow foam (295 mg). MS (ESI$^-$): 343.0 ([M–H]$^-$).

Example 16

2,4-Dichloro-N-(2-isopropyl-pyrimidin-4-yl)-6-methyl-benzenesulfonamide

This material was obtained in analogy to example 13 from 2-isopropyl-pyrimidin-4-ylamine (0.15 g) and 2,4-dichloro-6-methyl-benzenesulfonyl chloride (0.284 g) as a light yellow powder (87 mg). MS (ESI$^-$): 358.0 ([M–H]$^-$).

Example 17

2,3-Dichloro-N-(2-isopropyl-pyrimidin-4-yl)-benzenesulfonamide

This material was obtained in analogy to example 13 from 2-isopropyl-pyrimidin-4-ylamine (0.15 g) and 2,3-dichlorobenzenesulfonyl chloride (0.268 g) as a light yellow powder (110 mg). MS (ESI$^-$): 343.9 ([M–H]$^-$).

Example 18

4,5-Dichloro-thiophene-2-sulfonic acid (2-isopropyl-pyrimidin-4-yl)-amide

This material was obtained in analogy to example 13 from 2-isopropyl-pyrimidin-4-ylamine (0.15 g) and 4,5-dichlorothiophene-2-sulfonyl chloride (0.275 g) as a light yellow foam (28 mg). MS (ESI$^-$): 350.0 ([M–H]$^-$).

Example 19

5-Pyridin-2-yl-thiophene-2-sulfonic acid (2-isopropyl-pyrimidin-4-yl)-amide

This material was obtained in analogy to example 13 from 2-isopropyl-pyrimidin-4-ylamine (0.2 g) and 5-pyridin-2-yl-thiophene-2-sulfonyl chloride (0.379 g) as a light yellow foam (24 mg). MS (ESI$^-$): 359.0 ([M–H]$^-$).

Example 20

3-Chloro-N-(2-isopropyl-pyrimidin-4-yl)-2-methyl-benzenesulfonamide

This material was obtained in analogy to example 13 from 2-isopropyl-pyrimidin-4-ylamine (0.13 g) and 3-chloro-2-methyl-benzenesulfonyl chloride (0.2 g) as a light yellow foam (72 mg). MS (ESI$^-$): 324.1 ([M–H]$^-$).

Example 21

N-(2-Isopropyl-pyrimidin-4-yl)-3-trifluoromethyl-benzenesulfonamide

This material was obtained in analogy to example 13 from 2-isopropyl-pyrimidin-4-ylamine (0.2 g) and 3-trifluoromethyl-benzenesulfonyl chloride (0.357 g) as a light yellow foam (62 mg). MS (ESI$^-$): 344.0 ([M–H]$^-$).

Example 22

N-(2-Isopropyl-pyrimidin-4-yl)-2-trifluoromethyl-benzenesulfonamide

This material was obtained in analogy to example 13 from 2-isopropyl-pyrimidin-4-ylamine (0.2 g) and 2-trifluoromethyl-benzenesulfonyl chloride (0.357 g) as a light yellow powder (60 mg). MS (ESI$^-$): 344.1 ([M–H]$^-$).

Example 23

5-Chloro-thiophene-2-sulfonic acid (2-isopropyl-pyrimidin-4-yl)-amide

This material was obtained in analogy to example 13 from 2-isopropyl-pyrimidin-4-ylamine (0.2 g) and 5-chlorothiophene-2-sulfonyl chloride (0.316 g) as a light yellow powder (49 mg). MS (ESI$^-$): 316.0 ([M–H]$^-$).

Example 24

N-(2-Isopropyl-pyrimidin-4-yl)-4-trifluoromethyl-benzenesulfonamide

This material was obtained in analogy to example 13 from 2-isopropyl-pyrimidin-4-ylamine (0.2 g) and 4-trifluoromethyl-benzenesulfonyl chloride (0.357 g) as a light brown foam (211 mg). MS (ESI$^-$): 344.1 ([M–H]$^-$).

Example 25

Piperidine-1-sulfonic acid (2-isopropyl-pyrimidin-4-yl)-amide

This material was obtained in analogy to example 13 from 2-isopropyl-pyrimidin-4-ylamine (0.2 g) and piperidine-1-sulfonyl chloride (0.295 g) with the exception that the coupling reaction was allowed to proceed at an elevated temperature of 105° C. The desired product was obtained as a light yellow foam (139 mg). MS (ESI$^-$): 283.1 ([M–H]$^-$).

Example 26

Naphthalene-2-sulfonic acid (2-isopropyl-pyrimidin-4-yl)-amide

This material was obtained in analogy to example 13 from 2-isopropyl-pyrimidin-4-ylamine (0.13 g) and naphthalene-2-sulfonyl chloride (0.344 g) with the following modification: Pyridine was replaced by THF (5 mL) and potassium carbonate (0.144 g) was used as a base in this reaction that was allowed to proceed under reflux conditions for 24 hours.

After cooling, the mixture was filtered, evaporated in vacuo and the product was isolated by flash chromatography. The desired product was obtained as a yellow foam (53 mg). MS (ESI$^-$): 326.2 ([M–H]$^-$).

Example 27

Biphenyl-4-sulfonic acid (2-isopropyl-pyrimidin-4-yl)-amide

This material was obtained in analogy to example 13 from 2-isopropyl-pyrimidin-4-ylamine (0.13 g) and biphenyl-4-sulfonyl chloride (0.383 g) with the following modification: Pyridine was replaced by dioxane (5 mL) and potassium carbonate (0.144 g) was used as a base in this reaction that was allowed to proceed at 90° C. for 12 hours. After cooling, the mixture was filtered, evaporated in vacuo and the product was isolated by flash chromatography. The desired product was obtained as a yellow foam (31 mg). MS (ESI$^-$): 352.2 ([M–H]$^-$).

Example 28

2,5-Difluoro-N-(2-isopropyl-pyrimidin-4-yl)-benzenesulfonamide

This material was obtained in analogy to example 13 from 2-isopropyl-pyrimidin-4-ylamine (0.13 g) and 2,5-difluoro-benzenesulfonyl chloride (0.322 g) with the following modification: Pyridine was replaced by THF (5 mL) and potassium carbonate (0.144 g) was used as a base in this reaction that was allowed to proceed under reflux conditions for 12 hours. After cooling, the mixture was filtered, evaporated in vacuo and the product was isolated by flash chromatography. The desired product was obtained as a yellow foam (78 mg). MS (ESI$^-$): 312.0 ([M–H]$^-$).

Example 29

N-(2-Isopropyl-pyrimidin-4-yl)-3,4-dimethoxy-benzenesulfonamide

This material was obtained in analogy to example 13 from 2-isopropyl-pyrimidin-4-ylamine (0.13 g) and 3,3-dimethoxy-benzenesulfonyl chloride (0.359 g) with the following modification: Pyridine was replaced by THF (5 mL) and potassium carbonate (0.144 g) was used as a base in this reaction that was allowed to proceed under reflux conditions for 12 hours. After cooling, the mixture was filtered, evaporated in vacuo and the product was isolated by flash chromatography. The desired product was obtained as a yellow foam (21 mg). MS (ESI$^-$): 336.1 ([M–H]$^-$).

Example 30

N-(2-tert-Butyl-pyrimidin-4-yl)-3,4-dichloro-benzenesulfonamide

Step A:] 2-tert-Butyl-pyrimidin-4-ylamine

This material was obtained in analog to example 13, step A] from tert-butylcarbamidine hydrochloride (3.0 g) and 3-ethoxyacrylonitrile (2.2. mL) as a yellow foam (2.28 g). MS (EI): 151.0 (M$^+$), 136.0 ([M-CH$_3$]$^+$).

Step B]: N-(2-tert-Butyl-pyrimidin-4-yl)-3,4-dichloro-benzenesulfonamide

This material was obtained in analogy to example 13, step B] from 2-tert-butyl-pyrimidin-4-ylamine (0.15 g) and 3,3-dichloro-benzenesulfonyl chloride (0.244 g) as a white foam (0.134 g). MS (ESI$^-$): 357.9 ([M–H]$^-$).

Example 31

N-(2-tert-Butyl-pyrimidin-4-yl)-5-fluoro-2-methyl-benzenesulfonamide

This material was obtained in analogy to example 30 from 2-tert-butyl-pyrimidin-4-ylamine (0.15 g) and 5-fluoro-2-methyl-benzenesulfonyl chloride (0.21 g) as a light brown foam (118 mg). MS (ESI$^-$): 322.2 ([M–H]$^-$).

Example 32

Naphthalene-2-sulfonic acid (2-tert-butyl-pyrimidin-4-yl)-amide

This material was obtained in analogy to example 30 from 2-tert-butyl-pyrimidin-4-ylamine (0.15 g) and naphthalene-2-sulfonyl chloride (0.23 g) as a light yellow foam (141 mg). MS (ESI$^-$): 340.1 ([M–H]$^-$).

Example 33

N-(2-tert-Butyl-pyrimidin-4-yl)-2,5-difluoro-benzenesulfonamide

This material was obtained in analogy to example 30 from 2-tert-butyl-pyrimidin-4-ylamine (0.15 g) and 2,5-difluoro-benzenesulfonyl chloride (0.21 g) as a light brown foam (156 mg). MS (ESI$^-$): 326.2 ([M–H]$^-$).

Example 34

N-(2-tert-Butyl-pyrimidin-4-yl)-4-(1.3-oxazol-5-yl)-benzenesulfonamide

This material was obtained in analogy to example 30 from 2-tert-butyl-pyrimidin-4-ylamine (0.2 g) and 4-(1.3-oxazol-5-yl)-benzenesulfonyl chloride (0.322 g) as a white foam (104 mg). MS (ESI$^-$): 357.2 ([M–H]$^-$).

Example 35

3-Chloro-N-(2-ethyl-pyrimidin-4-yl)-2-methyl-benzenesulfonamide

Step A]: 2-Ethyl-pyrimidin-4-ylamine

This intermediate was made according to example 2, step A] via the alternative preparation method from propionamidine hydrochloride (1.45 g, obtained from propionitrile in analogy to Synth. Commun. 12 (13), 1982, 989-993 and Tetrahedron Lett. 31 (14), 1990, 1969-1972) and 2-chloro-acrylonitrile (1.17 mL). 2-Ethyl-pyrimidin-4-ylamine was obtained as a light brown solid (0.89 g): $^1$H NMR ($\delta$, DMSO-d$_6$): 7.96 (d, 1H), 6.68 (br s, 2H), 6.21 (s, 1H), 2.55 (q, 2H, 1.18 (t, 3H).

Step B] 3-Chloro-N-(2-ethyl-pyrimidin-4-yl)-2-methyl-benzenesulfonamide

This compound was obtained according to example 2, step B] from 2-ethyl-pyrimidin-4-ylamine (0.25 g), and 3-chloro-2-methyl-benzenesulfonyl chloride (0.55 g) as a colorless solid (86 mg). MS (ESI⁻): 310.0 ([M−H]⁻).

Example 36

2,4-Dichloro-N-(2-ethyl-pyrimidin-4-yl)-6-methyl-benzenesulfonamide

This material was obtained in analogy to example 35 from 2-ethyl-pyrimidin-4-ylamine (0.19 g) and 2,4-dichloro-6-methyl-benzenesulfonyl chloride (0.48 g) as a light brown solid (78 mg). MS (ESI): 346.0 (MH⁺).

Example 37

4-Chloro-N-(2-ethyl-pyrimidin-4-yl)-2,5-dimethyl-benzenesulfonamide

This material was obtained in analogy to example 35 from 2-ethyl-pyrimidin-4-ylamine (0.19 g) and 4-chloro-2,5-dimethyl-benzenesulfonyl chloride (0.423 g) as a light brown solid (59 mg). MS (ESI): 326.1 (MH⁺).

Example 38

3-Chloro-N-(2-cyclobutyl-pyrimidin-4-yl)-2-methyl-benzenesulfonamide

Step A]: 2-Cyclobutyl-pyrimidin-4-ylamine

This intermediate was made according to example 2, step A] method from cyclobutanecarboxamidine hydrochloride (0.3 g, obtained from cyclobutanecarbonitrile in analogy to Synth. Commun. 12 (13), 1982, 989-993 and Tetrahedron Lett. 31 (14), 1990, 1969-1972) and 3-ethoxy-acrylonitrile (0.3 g). 2-Cyclobutyl-pyrimidin-4-ylamine was obtained as a light brown solid (0.26 g): ¹H NMR (δ, DMSO-d₆): 7.98 (d, 1H), 6.66 (br s, 2H), 6.21 (s, 1H), 3.35-3-37 (m, 1H), 2.33-2.23 (m, 2H), 2.19-2.12 (m, 2H), 1.99-1.88 (m, 1H), 1.82-1.74 (m, 1H).

Step B] 3-Chloro-N-(2-cyclobutyl-pyrimidin-4-yl)-2-methyl-benzenesulfonamide This compound was obtained according to example 2, step B] from 2-cyclobutyl-pyrimidin-4-ylamine (0.15 g), and 3-chloro-2-methyl-benzenesulfonyl chloride (0.27 g) as a light brown solid (47 mg). MS (ESI): 338.1 (MH⁺).

Example 39

Naphthalene-2-sulfonic acid (2-cyclobutyl-pyrimidin-4-yl)-amide

This material was obtained in analogy to example 38 from 2-cyclobutyl-pyrimidin-4-ylamine (0.19 g) and naphthalene-2-sulfonyl chloride (0.27 g) as an orange solid (53 mg). MS (ESI⁻): 338.3 ([M−H]⁻).

Example 40

5-Pyridin-2-yl-thiophene-2-sulfonic acid (2-cyclobutyl-pyrimidin-4-yl)-amide This material was obtained in analogy to example 38 from 2-cyclobutyl-pyrimidin-4-ylamine (0.25 g) and 5-pyridin-2-yl-thiophene-2-sulfonyl chloride (0.47 g) as a light brown solid (36 mg). MS (ESI): 373.1 (MH⁺).

Example 41

2,4-Dichloro-N-(2-cyclobutyl-pyrimidin-4-yl)-6-methyl-benzenesulfonamide

This material was obtained in analogy to example 38 from 2-cyclobutyl-pyrimidin-4-ylamine (0.144 g) and 2,4-dichloro-6-methyl-benzenesulfonyl chloride (0.3 g) as a light brown solid (36 mg). MS (ESI): 372.1 (MH⁺).

Example 42

3,4-Dichloro-N-(2-methoxymethyl-pyrimidin-4-yl)-benzenesulfonamide

Step A]: 2-Methoxymethyl-pyrimidin-4-ylamine

2-Methoxymethyl-pyrimidin-4-ylamine (which has been described in the patent literature earlier in BE641253, 1964, Ciba Ltd.) was made according to example 2, step A] via the alternative method from known 2-methoxy-acetamidine hydrochloride (0.3 g, obtained from 2-methoxyacetonitrile in analogy to Synth. Commun. 12 (13), 1982, 989-993 and Tetrahedron Lett. 31 (14), 1990, 1969-1972) and 2-chloro-acrylonitrile (0.2 mL). 2-Methoxymethyl-pyrimidin-4-ylamine was obtained as an off-white solid (0.11 g): ¹H NMR (δ, CDCl₃): 8.22 (d, 1H), 6.32 (d, 1H), 4.98 (br s, 2H), 4.49 (s, 2H), 3.50 (s, 3H). MS (ESI): 140.3 (MH⁺).

Step B] 3,4-Dichloro-N-(2-methoxymethyl-pyrimidin-4-yl)-benzenesulfonamide This compound was obtained in analogy to example 2, step B] from 2-methoxymethyl-pyrimidin-4-ylamine (50 mg), and 3,4-dichlorobenzenesulfonyl chloride (111 mg) as a light yellow solid (10 mg). MS (ESI): 348.3 (MH⁺).

Example 43

3-Chloro-N-(2-cyclopropylmethoxymethyl-pyrimidin-4-yl)-2-methyl-benzenesulfonamide

Step A]: 2-Cyclopropylmethoxymethyl-pyrimidin-4-ylamine

Hydroxymethylcyclopropane (0.17 g) was dissolved in THF (2 mL) and at 0° C. sodium hydride dispersion (55% in oil, 0.1 g) was added. The mixture was allowed to stir for 30 minutes and subsequently, a solution of 2-chloromethyl-pyrimidin-4-ylamine (0.2 g, Eur. Pat. Appl. EP 61318 A2, 1982; Eur. Pat. Appl. 60094 A2, 1982) in THF (7 mL) was added dropwise. The resulting mixture was heated to reflux for 2 hours, cooled and water was added. The mixture was extracted with ethyl acetate and the organic layers were combined, dried over Na₂SO₄, filtered and evaporated. The residue was purified by flash chromatography (ethyl acetate/methanol 9:1) to give 2-cyclopropylmethoxymethylpyrimidin-4-ylamine as colorless solid (54 mg). $^1$H NMR ($\delta$, CDCl$_3$): 8.22 (d, 1H), 6.32 (d, 1H), 4.98 (br s, 2H), 4.58 (s, 2H), 3.46 (d, 2H), 1.21-1.12 (m, 1H), 0.59-0.53 (m, 2H), 0.27-0.24 (m, 2H). MS (ESI): 180.3 (MH$^+$).

Step B] 3-Chloro-N-(2-cyclopropylmethoxymethyl-pyrimidin-4-yl)-2-methyl-benzenesulfonamide This compound was obtained in analogy to example 2, step B] from 2-cyclopropylmethoxymethyl-pyrimidin-4-ylamine (54 mg), and 2-chloro-3-methyl-benzenesulfonyl chloride (81 mg) as a light yellow solid (13 mg). MS (ESI): 368.0 (MH$^+$).

Example 44

3-Chloro-2-methyl-N-(2-morpholin-4-ylmethyl-pyrimidin-4-yl)-benzenesulfonamide

Step A]:
2-Morpholin-4-ylmethyl-pyrimidin-4-ylamine

Following a procedure from J. Chem. Soc. Perkin. Trans. I, 1996, 2925, 2-chloromethyl-pyrimidin-4-ylamine (0.35 g, Eur. Pat. Appl. EP 61318 A2, 1982; Eur. Pat. Appl. 60094 A2, 1982) was dissolved in ethanol (10 mL) and triethylamine (0.51 mL) and morpholine (0.21 mL) were added. The mixture was heated to reflux for 48 hours and was then allowed to cool and evaporated in vacuo. The residue was dissolved in ethyl acetate and washed with 3N NaOH saturated with NaCl. The aqueous layer was subsequently re-extracted 5 times with ethyl acetate and the combined organic layers were dried over Na$_2$SO$_4$, filtered and evaporated. Flash chromatography (ethyl acetate/methanol 8:2) furnished the desired product 2-morpholin-4-ylmethyl-pyrimidin-4-ylamine as a light brown solid (0.23 g). $^1$H NMR ($\delta$, DMSO-d$_6$): 7.99 (d, 1H), 6.79 (br s, 2H), 6.28 (d, 1H), 3.56-3.53 (m, 4H, 3.36 (s, 2H), 2.46-2.43 (m, 4H). MS (ESI): 194.9 (MH$^+$).

Step B] 3-Chloro-2-methyl-N-(2-morpholin-4-ylmethyl-pyrimidin-4-yl)-benzenesulfonamide This compound was obtained in analogy to example 2, step B] from 2-morpholin-4-ylmethyl-pyrimidin-4-ylamine (230 mg), and 2-chloro-3-methyl-benzenesulfonyl chloride (319 mg) as a light yellow solid (65 mg). MS (ESI): 383.1 (MH$^+$).

Example 45

Naphthalene-2-sulfonic acid (2,6-dimethyl-pyrimidin-4-yl)-amide

This material was obtained in analogy to example 1 from 2,6-dimethyl-pyrimidin-4-ylamine (0.1 g, commercially available) and naphthalene-2-sulfonyl chloride (0.185 g) as a white foam (119 mg). MS (ESI$^-$): 312.0 ([M–H]$^-$).

Example 46

3-Chloro-N-(2-cyclopropyl-pyrimidin-4-yl)-2-N-dimethyl-benzenesulfonamide

3-Chloro-N-(2-cyclopropyl-pyrimidin-4-yl)-2-methyl-benzenesulfonamide (80 mg, example 2) was dissolved in DMF (2 mL) under argon at RT and cesium carbonate (121 mg) was added. After 20 minutes, methyl iodide (46 mg, 0.02 mL) was added dropwise and the resulting mixture was allowed to stir for 2 hours. The reaction mixture was poured into ice/water saturated with NaCl and the product was extracted into ethyl acetate. The organic layer was washed with brine, dried over Na$_2$SO$_4$, filtered and evaporated. The residue was purified by flash chromatography (gradient of ethyl acetate in heptane) to give—after drying in vacuo—3-chloro-N-(2-cyclopropyl-pyrimidin-4-yl)-2-N-dimethyl-benzenesulfonamide as the main product (50 mg, colorless oil). MS (ESI): 338.1 (MH$^+$).

As a side product of this reaction, 3-chloro-N-[2-cyclopropyl-3-methyl-3H-pyrimidin-(4E)-ylidene]-2-methyl-benzenesulfonamide was also isolated as a white foam (11 mg). MS (ESI): 338.0 (MH$^+$).

Example 47

3,4-Dichloro-N-(2-isopropyl-pyrimidin-4-yl)-N-methyl-benzenesulfonamide

This material was obtained in analogy to example 46 from 3,4-dichloro-N-(2-isopropyl-pyrimidin-4-yl)-benzenesulfonamide (76 mg, example 14) by treatment with cesium carbonate (107 mg) and methyl iodide (40 mg) in DMF (2 mL). 3,4-Dichloro-N-(2-isopropyl-pyrimidin-4-yl) N-methyl-benzenesulfonamide was obtained as a colorless oil (55 mg). MS (ESI): 360.1 (MH$^+$).

Example 48

3-Chloro-2-methyl-N-(2-phenyl-pyrimidin-4-yl)-benzenesulfonamide

This material was obtained in analogy to example 1 from 2-phenyl-pyrimidin-4-ylamine (134 mg, prepared as described in example 2, step A] according to Singh and Lesher, J. of Heterocyclic Chem. 1977, 14 (8), 1413-1414) and 2-chloro-3-methyl-benzenesulfonyl chloride (194 mg) as a colorless solid (60 mg). MS (ESI): 360.3 (MH$^+$).

Example 49

3-Chloro-2-methyl-N-[2-(2-methyl-thiazol-4-yl)-pyrimidin-4-yl]-benzenesulfonamide Step A]
2-(2-Methyl-thiazol-4-yl)-pyrimidin-4-ylamine This material was obtained as described in example 2, step A] from 2-ethyl-thiazole-4-carboxamidine hydrochloride (3 g) by treatment with sodium ethoxide (3.13 mL of a 5.4 M solution) and 3-ethoxyacrylonitrile (1.73 mL) to give 2-(2-ethyl-thiazol-4-yl)-pyrimidin-4-ylamine (2.56 g) as a brown solid. MS (ESI): 193.3 (MH$^+$).

Step B] 3-Chloro-2-methyl-N-[2-(2-methyl-thiazol-4-yl)-pyrimidin-4-yl]-benzenesulfonamide This material was obtained in analogy to example 1 from 2-(2-methyl-thiazol-4-yl)-pyrimidin-4-ylamine (179 mg) and 2-chloro-3-methyl-benzenesulfonyl chloride (200 mg) as a light yellow foam (54 mg). MS (ESI$^-$): 379.0 ([M–H]$^-$).

Example 50

3-Chloro-N-(2-methoxymethyl-pyrimidin-4-yl)-2-methyl-benzenesulfonamide

This material was obtained in analogy to example 42, step B] from 2-methoxymethyl-pyrimidin-4-ylamine (obtained in example 42, step A], 50 mg) and 3-chloro-2-methyl-benzenesulfonyl chloride (97 mg) as a light yellow solid (11 mg). MS (ESI): 328.1 (MH$^+$).

Example 51

Naphthalene-2-sulfonic acid (2,5,6-trimethyl-pyrimidin-4-yl)-amide

Step A]: 2,5,6-Trimethyl-pyrimidin-4-ylamine

4-Chloro-2,5,6-trimethyl-pyrimidine (143 g, CAS 34916-70-6, see Curd, R., J. Chem. Soc. (1946), 362, 365) were treated with 100% NH$_3$ (900 g) at 100-150° C. for 6 hours. The reaction mixture was cooled and evaporated. The residue was dissolved in water (200 mL) and extracted with CHCl$_3$. The organic layer was separated and the aqueous layer was saturated with Na$_2$CO$_3$. The aqueous solution was extracted four times with more CHCl$_3$ and the combined organic extracts were evaporated to give 30 g of a residue. This residue was dissolved in ethyl acetate and precipitated with petroleum ether. The solid was filtered and dried to give 17 g of 2,5,6-trimethyl-pyrimidin-4-ylamine. Mp: 187° C.

Step B] Naphthalene-2-sulfonic acid (2,5,6-trimethyl-pyrimidin-4-yl)-amide

This material was obtained in low yield in analogy to example 1 from 2,5,6-trimethyl-pyrimidin-4-ylamine (100 mg) and naphthalene-2-sulfonyl chloride (165 mg) to give naphthalene-2-sulfonic acid (2,5,6-trimethyl-pyrimidin-4-yl)-amide as a light brown foam (8 mg). MS (ESI$^-$): 326.3 ((M–H)$^-$).

Example 52

4,5-Dichloro-2-fluoro-N-(2-isopropyl-pyrimidin-4-yl)-benzenesulfonamide

This material was obtained in analogy to example 13 from 2-isopropyl-pyrimidine-4-ylamine (200 mg) and 4,5-dichloro-2-fluoro-benzenesulfonyl chloride (384 mg) as an orange powder (107 mg). MS (ESI$^-$): 362.0 ((M–H)$^-$).

Example 53

2,4-Difluoro-N-(2-isopropyl-pyrimidin-4-yl)-benzenesulfonamide

This material was obtained in analogy to example 13 from 2-isopropyl-pyrimidine-4-ylamine (200 mg) and 2,4-difluoro-benzenesulfonyl chloride (300 mg) as a yellow powder (68 mg). MS (ESI$^-$): 312.0 ((M–H)$^-$).

Example 54

2-Chloro-N-(2-isopropyl-pyrimidin-4-yl)-benzenesulfonamide

This material was obtained in analogy to example 13 from 2-isopropyl-pyrimidine-4-ylamine (200 mg) and 2-chloro-benzenesulfonyl chloride (308 mg) as a light yellow foam (127 mg). MS (ESI$^-$): 310.0 ((M–H)$^-$).

Example 55

4-Chloro-N-(2-isopropyl-pyrimidin-4-yl)-benzenesulfonamide

This material was obtained in analogy to example 13 from 2-isopropyl-pyrimidine-4-ylamine (200 mg) and 4-chloro-benzenesulfonyl chloride (308 mg) as a light yellow foam (127 mg). MS (ESI$^-$): 310.0 ((M–H)$^-$).

Example 56

3-Chloro-N-(2-isopropyl-pyrimidin-4-yl)-benzenesulfonamide

This material was obtained in analogy to example 13 from 2-isopropyl-pyrimidine-4-ylamine (200 mg) and 3-chloro-benzenesulfonyl chloride (308 mg) as a light yellow foam (175 mg). MS (ESI$^-$): 310.0 ((M–H)$^-$).

Example 57

2,4-Dichloro-N-(2-isopropyl-pyrimidin-4-yl)-benzenesulfonamide

This material was obtained in analogy to example 13 from 2-isopropyl-pyrimidine-4-ylamine (200 mg) and 2,4-dichloro-benzenesulfonyl chloride (358 mg) as an orange powder (163 mg). MS (ESI$^-$): 344.0 ((M–H)$^-$).

Example 58

2,4-Dichloro-N-(2-isopropyl-pyrimidin-4-yl)-5-methyl-benzenesulfonamide

This material was obtained in analogy to example 13 from 2-isopropyl-pyrimidine-4-ylamine (200 mg) and 2,4-dichloro-5-methyl-benzenesulfonyl chloride (378 mg) as an orange powder (194 mg). MS (ESI$^-$): 358.0 ((M–H)$^-$).

Example 59

2,5-Dichloro-N-(2-isopropyl-pyrimidin-4-yl)-benzenesulfonamide

This material was obtained in analogy to example 13 from 2-isopropyl-pyrimidine-4-ylamine (200 mg) and 2,5-dichloro-benzenesulfonyl chloride (358 mg) as an orange powder (160 mg). MS (ESI$^-$): 344.0 ((M–H)$^-$).

Example 60

3-Bromo-5-chloro-thiophene-2-sulfonic acid (2-isopropyl-pyrimidin-4-yl)-amide This material was obtained in low yield in analogy to example 13 from 2-isopropyl-pyrimidine-4-ylamine (200 mg) and 3-bromo-5-chloro-thiophene-2-sulfonyl chloride (431 mg) as an orange powder (12 mg). MS (ESI⁻): 393.8 ((M−H)⁻).

Example 61

2,4-Dichloro-N-(2-cyclopropyl-pyrimidin-4-yl)-6-methyl-benzenesulfonamide

This material was obtained in analogy to example 2 from 2-cyclopropyl-pyrimidine-4-ylamine (190 mg) and 2,4-dichloro-6-methyl-benzenesulfonyl chloride (438 mg) as a light brown solid (75 mg). MS (ESI): 358.1 (MH⁺).

Example 62

4-Chloro-N-(2-cyclopropyl-pyrimidin-4-yl)-2,5-dimethyl-benzenesulfonamide

This material was obtained in analogy to example 2 from 2-cyclopropyl-pyrimidine-4-ylamine (190 mg) and 4-chloro-2,5-dimethylbenzenesulfonyl chloride (403 mg) as a light brown solid (73 mg). MS (ESI): 338.0 (MH⁺).

Example 63

N-(2-Cyclopropyl-pyrimidin-4-yl)-2,4-dimethoxy-benzenesulfonamide

This material was obtained in low yield in analogy to example 2 from 2-cyclopropyl-pyrimidine-4-ylamine (150 mg) and 2,4-dimethoxy-benzenesulfonyl chloride (315 mg) as a colorless solid (13 mg). MS (ESI⁻): 334.1 ((M−H)⁻).

Example 64

3-Chloro-N-(2-cyclopentyl-pyrimidin-4-yl)-2-methyl-benzenesulfonamide

Step A]: 2-Cyclopentyl-pyrimidin-4-ylamine

This material was obtained in analogy to example 2, step A] via the alternative preparation method from cyclopentanecarboxamidine hydrochloride (CAS 68284-02-6) (500 mg) and 2-chloroacrylonitrile (324 mg) to give 2-cyclopentyl-pyrimidin-4-ylamine as an amorphous glass (142 mg). MS (ESI): 164.6 (MH⁺). This material was contaminated with several side products that could not be identified.

Step B]: 3-Chloro-N-(2-cyclopentyl-pyrimidin-4-yl)-2-methyl-benzenesulfonamide

This material was obtained in analogy to example 2, step B] from 2-cyclopentyl-pyrimidin-4-ylamine (158 mg) and 3-chloro-2-methyl-benzenesulfonyl chloride (261 mg) as a light brown solid (75 mg). MS (ESI): 352.4 (MH⁺).

Example 65

5-Phenyl-thiophene-2-sulfonic acid (2-cyclopropyl-pyrimidin-4-yl)-amide

This material was obtained in analogy to example 2 from 2-cyclopropyl-pyrimidin-4-ylamine (100 mg) and 5-phenyl-thiophene-2-sulfonyl chloride (203 mg, CAS 97272-02-1, made according to Sone et al., Bull. Chem. Soc. J. (1985), 58(3), 1063) as a colorless solid (33 mg). MS (ESI⁻): 356.3 ((M−H)⁻).

Example 66

3-Chloro-N-(2-cyclopropylmethoxy-pyrimidin-4-yl)-2-methyl-benzenesulfonamide Step A]: 2-Cyclopropylmethoxy-pyrimidin-4-ylamine Cyclopropylmethanol (724 mg) was dissolved in DMF (4 mL) and treated with sodium hydride (401 mg, 60% in mineral oil) at 0° C. for 30 minutes. Then, a solution of 4-amino-2-chloro-pyrimidine (260 mg, CAS 7461-50-9 or made according to J. Am. Chem. Soc. 1930, 52, 1152-1157) in DMF (4 mL) was added drop by drop. The mixture was stirred at room temperature for 1 hour and then allowed to stir at 50° C. over night. The mixture was poured into water and the mixture was saturated with NaCl. The aqueous solution was then extracted with ethyl acetate and the organic layer was washed with brine, dried over Na₂SO₄ and evaporated to dryness. The residue was purified by flash chromatography on silica gel using a gradient of ethyl acetate in heptane as an eluant. The desired product was obtained as a light yellow oil (169 mg). MS (EI): 166.2 (M+H⁺).

Step B]: 3-Chloro-N-(2-cyclopropylmethoxy-pyrimidin-4-yl)-2-methyl-benzenesulfonamide This material was obtained low yield in analogy to example 1 from 2-cyclopropylmethoxy-pyrimidin-4-ylamine (220 mg) and 3-chloro-2-methyl-benzenesulfonyl chloride (161 mg) to give the desired product as a light yellow foam (14 mg). MS (ESI⁻): 352.1 ((M−H)⁻).

Example 67

2-[(3,4-Dichloro-benzenesulfonyl)-(2-isopropyl-pyrimidin-4-yl)-amino]-N,N-dimethyl-acetamide 3,4-Dichloro-N-(2-isopropyl-pyrimidin-4-yl)-benzenesulfonamide (80 mg, example 14) was dissolved in DMF (1 mL) and treated with cesium carbonate (113 mg). To the mixture was added 2-chloro-N,N-dimethylacetamide (37 mg) and the resulting suspension was allowed to stir at room temperature for 48 hours and then at 80° C. for 24 hours. The mixture was diluted with ethyl acetate, washed with brine, dried over Na₂SO₄ and evaporated to dryness. The residue was purified by flash chromatography on silica gel using DCM/MeOH/NH₄OH 9:1:0.1 as an eluant. The desired product was obtained as a colorless glass (28 mg). MS (ESI): 431.3 (MH⁺).

Example 68

N-Benzyl-3-chloro-N-(2-cyclopropyl-pyrimidin-4-yl)-2-methyl-benzenesulfonamide This material was obtained in analogy to example 67 from 3-chloro-N-(2-cyclopropyl-pyrimidin-4-yl)-2-methyl-benzenesulfonamide (120 mg, example 2) using benzyl chloride (61 mg) as the alkylating agent. The desired material was obtained as a colorless oil (74 mg). MS (EI): 414.1 (M+H⁺).

Example 69

3-Chloro-N-cyclopropylmethyl-N-(2-cyclopropyl-pyrimidin-4-yl)-2-methyl-benzenesulfonamide This material was obtained in analogy to example 67 from 3-chloro-N-(2-cyclopropyl-pyrimidin-4-yl)-2-methyl-benzenesulfonamide (120 mg, example 2) using bromomethyl-cyclopropane (65 mg) as the alkylating agent. The desired material was obtained as a colorless oil (89 mg). MS (EI): 377 ($M^+$), 378.3 ($M+H^+$).

Example 70

3-Chloro-2-methyl-N-(6-phenyl-pyrimidin-4-yl)-benzenesulfonamide

This material was obtained in analogy to example 1 from 6-phenyl-pyrimidin-4-ylamine (97 mg, CAS 3435-29-8) and 3-chloro-2-methyl-benzenesulfonyl chloride (128 mg) to give the desired product as a light yellow foam (67 mg). MS ($ESI^-$): 358.0 (($M-H)^-$).

Example 71

A compound of formula I can be used in a manner known per se as the active ingredient for the production of tablets of the following composition:

| Per tablet | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example 72

A compound of formula I can be used in a manner known per se as the active ingredient for the production of capsules of the following composition:

| Per capsule | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

Example 73

Assay Procedures

Transient Expression and Partial Purification:

The cDNA encoding the human 11beta-HSD1 protein was cloned into the expression vector pcDNA3 (Stratagene). This construct (for details see Alex Odermatt et al.; J Biol Chem., 1999, Vol. 274, Issue 40, 28762-28770) was used to transiently express the protein in HEK293 cells (ATCC number: CRL-1573, described in Graham, F. L., Smiley, J., Russell, W. C., Nairn, R.; (1977)) using lipofectamine. 48 h after transfection cells were washed twice with ice-cold PBS (Phsophate buffered Saline). To 1 volume of cell suspension in PBS 2 volumes of ice-cold lysis buffer (50 mM Tris; pH7.5; 1 mM EDTA; 100 mM NaCl) were added. The cells were lysed by Potter-homogenization (20 strokes). The resulting homogenate was sonicated with a tip sonicator (10% output; 2×30 sec.) and cleared by a low speed centrifugation (10 min×9000 g; 4° C.). The microsomal fraction was collected by a high speed centrifugation (60 min×110,000 g). The resulting pellet was resuspended in storage buffer (20 mM Tris pH 7.5; 1 mM EDTA; 10% Glycerol) and the centrifugation was repeated. The resulting pellet containing the microsomal fraction was again taken up into storage buffer and aliquots were kept frozen in liquid nitrogen until use.

Generation of Stable Cell Lines Expressing 11beta-HSD1:

The same construct used for transient expression of human 11beta-HSD1 was also used to establish cell lines stably expressing the protein. Briefly, (HEK293) cells were transfected with 11beta-HSD1 construct using the lipofectamine reagent (Gibco BRL) according to the manufacturer's instruction. Two days after transfection, geneticin selection (0.8 mg/ml) was initiated and several stable clones were isolated. One clone was further used for pharmacological characterization.

Microsome Assay

Microsomes isolated from HEK293 cells transiently expressing human 11beta-HSD1 (for details see above) were incubated in assay buffer (100 mM NaCl; 1 mM EDTA; 1 mM EGTA; 1 mM MgCl; 250 mM Sucrose; 20 mM Tris pH 7.4; Cortisone 50-200 nM and NADPH 1 mM) together with different concentrations of test substances. After 60 min. of incubation at 37° C. the assay was stopped by heating to 80° C. (5 min.) and by addition of the inhibitor Carbenoxolone (1 μM). The amount of Cortisol produced in this assay was determined using a commercially available, ELISA-based Cortisol-detection kit (Distributed by Assay Design, Inc.). Inhibitors were characterized by there IC50 values, e.g. the concentration at which the production of cortisol was 50% reduced.

In this test preferred compounds as described above have IC50 values below 1000 nM; more preferred compounds have IC50 values below 100 nM. Most preferred compounds have IC50 values below 10 nM.

Cellular Assay

To measure the effect of inhibitors in intact cells HEK293 cells stably expressing human 11beta-HSD1 (see above) were cultivated in 96 well plates in DMEM. First inhibitors and 60 min later Cortisone was added to the cells. After 60 min of incubation at 37° C. in a 5% $CO_2$ atmosphere part of the medium was removed and the conversion from Cortisone to Cortisol was measured using a commercially available ELISA kit (Distributed by Assay Design, Inc.).

Results obtained in the microsome assay using representative compounds of the invention as the test compounds are shown in the following table:

| Compound | h 11-beta-HSD 1 $IC_{50}$ (nM) |
|---|---|
| Example 5 | 20 |
| Example 26 | 167 |

The invention claimed is:

1. A compound of the formula (I):

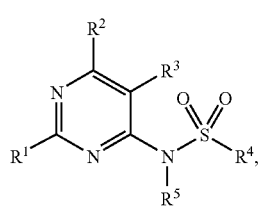

wherein:
R¹ is methyl, ethyl, cyclopropyl, cyclobutyl, isopropyl, tert.butyl, methoxymethyl, cyclopropylmethoxymethyl, 2-methyl-thiazolyl, morpholinylmethyl or phenyl;
R² is hydrogen, alkyl or aryl;
R³ is hydrogen, alkyl or aryl;
R⁴ is phenyl, naphthyl, thiophenyl, quinolyl, piperidyl, morpholyl or thiomorpholyl, wherein phenyl, naphthyl, thiophenyl, quinolyl, piperidyl, morpholyl and thiomorpholyl are optionally substituted with one or more substituents independently selected from alkyl, cycloalkyl, halogen, alkoxy, cyano, trifluoromethyl, aryl, arylalkyl, aryloxy, oxazolyl, pyridinyl, pyrimidinyl, pyrazolyl, imidazolyl and thiazolyl;
R⁵ is hydrogen, alkyl, aralkyl, cycloalkylalkyl or aminocarbonylalkyl;
and pharmaceutically acceptable salts and esters thereof; and, wherein
N-(2,6-dimethyl-4-pyrimidinyl)-benzenesulfonamide;
2-chloro-N-(2-methyl-4-pyrimidinyl)-p-toluenesulfonamide;
2, 4, 5-trichloro-N-(2,6-dimethyl-4-pyrimidinyl)-benzenesulfonamide; and
4-chloro-N-(2,6-dimethyl-pyrimidin-4-yl)-benzenesulfonamide are excluded.

2. The compound according to claim 1, wherein:
R² is hydrogen or alkyl;
R³ is hydrogen or alkyl; and
R⁵ is hydrogen or alkyl.

3. The compound according to claim 1, wherein R² is hydrogen.

4. The compound according to claim 1, wherein R² is methyl.

5. The compound according to claim 1, wherein R³ is hydrogen.

6. The compound according to claim 1, wherein R⁵ is hydrogen.

7. The compound according to claim 1, wherein R⁵ is methyl.

8. The compound according to claim 1, wherein R⁴ is phenyl, naphthyl, thiophenyl, quinolyl or piperidyl, wherein phenyl, naphthyl, thiophenyl, quinolyl and piperidyl are optionally substituted with one or more substituents independently selected from alkyl, halogen, alkoxy, trifluoromethyl, aryl, oxazolyl and pyridinyl.

9. The compound according to claim 1, wherein R⁴ is phenyl substituted with one or more substituents independently selected from alkyl, cycloalkyl, halogen, alkoxy, trifluoromethyl, phenyl and oxazolyl.

10. The compound according to claim 1, wherein R⁴ is phenyl, naphthyl, quinolyl or piperidyl.

11. The compound according to claim 1, wherein R⁴ is thiophenyl, morpholyl or thiomorpholyl, wherein thiophenyl, morpholyl and thiomorpholyl are optionally substituted with one or more substituents independently selected from alkyl, cycloalkyl, halogen, alkoxy, cyano, trifluoromethyl, aryl, arylalkyl, aryloxy, oxazolyl, pyridinyl, pyrimidinyl, pyrazolyl, imidazolyl and thiazolyl.

12. The compound according to claim 1, selected from the group consisting of:
3-Chloro-2-methyl-N-(2-methyl-pyrimidin-4-yl)-benzenesulfonamide;
3-Chloro-N-(2-cyclopropyl-pyrimidin-4-yl)-2-methyl-benzenesulfonamide;
N-(2-Cyclopropyl-pyrimidin-4-yl)-2,5-difluoro-benzenesulfonamide;
Naphthalene-2-sulfonic acid (2-cyclopropyl-pyrimidin-4-yl)-amide;
Biphenyl-4-sulfonic acid (2-cyclopropyl-pyrimidin-4-yl)-amide;
Quinoline-8-sulfonic acid (2-cyclopropyl-pyrimidin-4-yl)-amide;
N-(2-Cyclopropyl-pyrimidin-4-yl)-benzenesulfonamide;
N-(2-Cyclopropyl-pyrimidin-4-yl)-5-fluoro-2-methyl-benzenesulfonamide;
N-(2-Cyclopropyl-pyrimidin-4-yl)-3-methoxy-benzenesulfonamide;
N-(2-Cyclopropyl-pyrimidin-4-yl)-2-methoxy-5-methyl-benzenesulfonamide;
3-Chloro-N-(2-cyclopropyl-pyrimidin-4-yl)-4-methoxy-benzenesulfonamide;
5-Chloro-N-(2-cyclopropyl-pyrimidin-4-yl)-2-methoxy-benzenesulfonamide;
5-Fluoro-N-(2-isopropyl-pyrimidin-4-yl )-2-methyl-benzenesulfonamide;
3,4-Dichloro-N-(2-isopropyl-pyrimidin-4-yl)-benzenesulfonamide;
N-(2-Isopropyl-pyrimidin-4-yl)-4-(1,3-oxazol-5-yl)-benzenesulfonamide;
2,4-Dichloro-N-(2-isopropyl-pyrimidin-4-yl)-6-methyl-benzenesulfonamide;
2,3-Dichloro-N-(2-isopropyl-pyrimidin-4-yl)-benzenesulfonamide;
4,5-Dichloro-thiophene-2-sulfonic acid (2-isopropyl-pyrimidin-4-yl)-amide;
5-Pyridin-2-yl-thiophene-2-sulfonic acid (2-isopropyl-pyrimidin-4-yl)-amide;
3-Chloro-N-(2-isopropyl-pyrimidin-4-yl)-2-methyl-benzenesulfonamide;
N-(2-Isopropyl-pyrimidin-4-yl)-3-trifluoromethyl-benzenesulfonamide;
N-(2-Isopropyl-pyrimidin-4-yl)-2-trifluoromethyl-benzenesulfonamide;
5-Chloro-thiophene-2-sulfonic acid (2-isopropyl-pyrimidin-4-yl)-amide;
N-(2Isopropyl-pyrimidin-4-yl)-4-trifluoromethyl-benzenesulfonamide;
Piperidine-1 -sulfonic acid (2-isopropyl-pyrimidin-4-yl)-amide;
Naphthalene-2-sulfonic acid (2-isopropyl-pyrimidin-4-yl)-amide;

Biphenyl-4-sulfonic acid (2-isopropyl-pyrimidin-4-yl)-amide;
2,5-Difluoro-N-(2-isopropyl-pyrimidin-4-yl)-benzenesulfonamide;
N-(2-Isopropyl-pyrimidin-4-yl )-3,4-dimethoxy-benzenesulfonamide;
N-(2-tert-Butyl-pyrimidin-4-yl )-3,4-dichloro-benzenesulfonamide;
N-(2-tert-Butyl-pyrimidin-4-yl)-5-fluoro-2-methyl-benzenesulfonamide;
Naphthalene-2-sulfonic acid (2-tert-butyl-pyrimidin-4-yl)-amide;
N-(2-tert-Butyl-pyrimidin-4-yl)-2,5-difluoro-benzenesulfonamide;
N-(2-tert-Butyl-pyrimidin-4-yl)-4-(1.3-oxazol-5-yl)-benzenesulfonamide;
3-Chloro-N-(2-ethyl-pyrimidin-4-yl)-2-methyl-benzenesulfonamide;
2,4-Dichloro-N-(2-ethyl-pyrimidin-4-yl)-6-methyl-benzenesulfonamide;
4-Chloro-N-(2-ethyl-pyrimidin-4-yl )-2,5-dimethyl-benzenesulfonamide;
3-Chloro-N-(2-cyclobutyl-pyrimidin-4-yl)-2-methyl-benzenesulfonamide;
Naphthalene-2-sulfonic acid (2-cyclobutyl-pyrimidin-4-yl)-amide;
5-Pyridin-2-yl-thiophene-2-sulfonic acid (2-cyclobutyl-pyrimidin-4-yl)-amide;
2,4-Dichloro-N-(2-cyclobutyl-pyrimid in-4-yl)-6-methyl-benzenesulfonamide;
3,4-Dichloro-N-(2-methoxymethyl-pyrimidin-4-yl)-benzenesulfonamide; 3-Chloro-N-(2-cyclopropylmethoxymethyl-pyrimidin-4-yl)-2-methyl-benzenesulfonamide;
3-Chloro-2-methyl-N-(2-morpholin-4-ylmethyl-pyrimidin-4-yl)-benzenesulfonamide;
Naphthalene-2-sulfonic acid (2,6-dimethyl-pyrimidin-4-yl)-amide;
3-Chloro-N-(2-cyclopropyl-pyrimidin-4-yl)-2-N-dimethyl-benzenesulfonamide;
3,4-Dichloro-N-(2-isopropyl-pyrimidin-4-yl)-N-methyl-benzenesulfonamide;
3-Chloro-2-methyl-N-(2-phenyl-pyrimidin-4-yl)-benzenesulfonamide; and
3-Chloro-2-methyl-N-[2-(2-methyl-thiazol-4-yl)-pyrimidin-4-yl]-benzenesulfonamide.

13. The compound according to claim 1, selected from the group consisting of:

3-Chloro-N-(2-methoxymethyl-pyrimidin-4-yl )-2-methyl-benzenesulfonamide;
Naphthalene-2-sulfonic acid (2,5,6-trimethyl-pyrimidin-4-yl)-amide;
4,5-Dichloro-2-fluoro-N-(2-isopropyl-pyrimidin-4-yl)-benzenesulfonamide;
2,4-Difluoro-N-(2-isopropyl-pyrimidin-4-yl)-benzenesulfonamide;
2-Chloro-N-(2-isopropyl-pyrimidin-4-yl)-benzenesulfonamide;
4-Chloro-N-(2-isopropyl-pyrimidin-4-yl)-benzenesulfonamide;
3-Chloro-N-(2-isopropyl-pyrimidin-4-yl)-benzenesulfonamide;
2,4-Dichloro-N-(2-isopropyl-pyrimidin-4-yl)-benzenesulfonamide;
2,4-Dichloro-N-(2-isopropyl-pyrimidin-4-yl)-5-methyl-benzenesulfonamide;
2,5-Dichloro-N-(2-isopropyl-pyrimidin-4-yl)-benzenesulfonamide;
3-Bromo-5-chloro-thiophene-2-sulfonic acid (2-isopropyl-pyrimidin-4-yl)-amide;
2,4-Dichloro-N-(2-cyclopropyl-pyrimidin-4-yl)-6-methyl-benzenesulfonamide;
4-Chloro-N-(2-cyclopropyl-pyrimidin-4-yl)-2,5-dimethyl-benzenesulfonamide;
N-(2-Cyclopropyl-pyrimidin-4-yl)-2,4-dimethoxy-benzenesulfonamide;
3-Chloro-N-(2-cyclopentyl-pyrimidin-4-yl)-2-methyl-benzenesulfonamide;
5-Phenyl-thiophene-2-sulfonic acid (2-cyclopropyl-pyrimidin-4-yl)-amide;
3-Chloro-N-(2-cyclopropylmethoxy-pyrimidin-4-yl)-2-methyl-benzenesulfonamide;
2-[(3,4-Dichloro-benzenesulfonyl)-(2-isopropyl-pyrimidin-4-yl)-amino]-N, N-dimethyl-acetamide;
N-Benzyl-3-chloro-N-(2-cyclopropyl-pyrimidin-4-yl)-2-methyl-benzenesulfonamide;
3-Chloro-N-cyclopropylmethyl-N-(2-cyclopropyl-pyrimidin-4-yl)-2-methyl-benzenesulfonamide and
3-Chloro-2-methyl-N-(6-phenyl-pyrimidin-4-yl )-benzenesulfonamide.

14. The compound according to claim 1, selected from the group consisting of:

3-Chloro-2-methyl-N-(2-methyl-pyrimidin-4-yl)-benzenesulfonamide;
3-Chloro-N-(2-cyclopropyl-pyrimidin-4-yl)-2-methyl-benzenesulfonamide;
N-(2-Cyclopropyl-pyrimidin-4-yl)-2,5-difluoro-benzenesulfonamide;
Naphthalene-2-sulfonic acid (2-cyclopropyl-pyrimidin-4-yl)-amide;
Biphenyl-4-sulfonic acid (2-cyclopropyl-pyrimidin-4-yl)-amide;
5-Fluoro-N-(2-isopropyl-pyrimidin-4-yl )-2-methyl-benzenesulfonamide;
3,4-Dichloro-N-(2-isopropyl-pyrimidin-4-yl)-benzenesulfonamide;
N-(2-Isopropyl-pyrimidin-4-yl)-4-(1.3-oxazol-5-yl)-benzenesulfonamide;
2,4-Dichloro-N-(2-isopropyl-pyrimidin-4-yl)-6-methyl-benzenesulfonamide;
2,3-Dichloro-N-(2-isopropyl-pyrimidin-4-yl)-benzenesulfonamide;
5-Pyridin-2-yl-thiophene-2-sulfonic acid (2-isopropyl-pyrimidin-4-yl)-amideyes;
3-Chloro-N-(2-isopropyl-pyrimidin-4-yl)-2-methyl-benzenesulfonamide;
N-(2-Isopropyl-pyrimidin-4-yl)-3-trifluoromethyl-benzenesulfonamide;
N-(2-Isopropyl-pyrimidin-4-yl)-2-trifluoromethyl-benzenesulfonamide;
5-Chloro-thiophene-2-sulfonic acid (2-isopropyl-pyrimidin-4-yl)-amide;

N-(2-Isopropyl-pyrimidin-4-yl)-4-trifluoromethyl-benzenesulfonamide;

Naphthalene-2-sulfonic acid (2-isopropyl-pyrimidin-4-yl)-amide;

Biphenyl-4-sulfonic acid (2-isopropyl-pyrimidin-4-yl)-amide;

2,5-Difluoro-N-(2-isopropyl-pyrimidin-4-yl)-benzenesulfonamide;

N-(2-Isopropyl-pyrimidin-4-yl )-3,4-dimethoxy-benzenesulfonamide;

N-(2-tert-Butyl-pyrimidin-4-yl)-4-oxazol-5-yl-benzenesulfonamide;

3-Chloro-N-(2-ethyl-pyrimidin-4-yl)-2-methyl-benzenesulfonamide;

2,4-Dichloro-N-(2-ethyl-pyrimidin-4-yl)-6-methyl-benzenesulfonamide;

3-Chloro-N-(2-cyclobutyl-pyrimidin-4-yl)-2-methyl-benzenesulfonamide;

Naphthalene-2-sulfonic acid (2-cyclobutyl-pyrimidin-4-yl)-amide;

5-Pyridin-2-yl-thiophene-2-sulfonic acid (2-cyclobutyl-pyrimidin-4-yl)-amide;

2,4-Dichloro-N-(2-cyclobutyl-pyrimidin-4-yl)-6-methyl-benzenesulfonamide;

3-Chloro-N-(2-cyclopropyl-pyrimidin-4-yl)-2-N-dimethyl-benzenesulfonamide; and 3,4-Dichloro-N-(2-isopropyl-pyrimidin-4-yl)-N-methyl-benzenesulfonamide.

15. A process for the preparation of a compound according claim 1, comprising the reaction of a compound according to formula

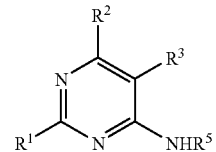

A in the presence of a compound according to formula

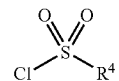

wherein $R^1$ to $R^5$ are defined as in claim 1.

16. A pharmaceutical composition comprising a therapeutically effective amount of a compound according to claim 1 and a therapeutically inert carrier.

17. A method for the treatment of diabetes, comprising the step of administering a therapeutically effective amount of a compound according to claim 1 to a patient in need thereof.

18. A method for the treatment of diabetes Type II, comprising the step of administering a therapeutically effective amount of a compound according to claim 1 to a patient in need thereof.

* * * * *